(12) United States Patent
Hamprecht et al.

(10) Patent No.: US 9,078,909 B2
(45) Date of Patent: Jul. 14, 2015

(54) TERTIARY AMINES, MEDICAMENTS CONTAINING SAID AMINES, USE THEREOF AND PROCESSES FOR THE PREPARATION THEREOF

(71) Applicants: Dieter Hamprecht, Pozzolengo (IT); Armin Heckel, Biberach an der Riss (DE); Joerg Kley, Mittelbiberach (DE)

(72) Inventors: Dieter Hamprecht, Pozzolengo (IT); Armin Heckel, Biberach an der Riss (DE); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 66 days.

(21) Appl. No.: 13/899,762

(22) Filed: May 22, 2013

(65) Prior Publication Data

US 2013/0316981 A1    Nov. 28, 2013

(30) Foreign Application Priority Data

May 25, 2012  (EP) .................................... 12169577

(51) Int. Cl.

| | | |
|---|---|---|
| *A61K 31/495* | (2006.01) | |
| *A61K 31/5377* | (2006.01) | |
| *A61K 31/541* | (2006.01) | |
| *A61K 45/06* | (2006.01) | |
| *C07D 401/12* | (2006.01) | |
| *C07D 401/14* | (2006.01) | |
| *C07D 405/14* | (2006.01) | |
| *C07D 409/14* | (2006.01) | |
| *C07D 417/14* | (2006.01) | |
| *C07D 471/08* | (2006.01) | |
| *C07D 453/02* | (2006.01) | |
| *A61K 31/675* | (2006.01) | |
| *C07F 9/6509* | (2006.01) | |
| *C07F 9/6558* | (2006.01) | |

(52) U.S. Cl.
CPC .............. *A61K 31/675* (2013.01); *A61K 31/495* (2013.01); *A61K 31/5377* (2013.01); *A61K 31/541* (2013.01); *A61K 45/06* (2013.01); *C07D 401/12* (2013.01); *C07D 401/14* (2013.01); *C07D 405/14* (2013.01); *C07D 409/14* (2013.01); *C07D 417/14* (2013.01); *C07D 453/02* (2013.01); *C07D 471/08* (2013.01); *C07F 9/65583* (2013.01); *C07F 9/650958* (2013.01)

(58) Field of Classification Search
CPC .............. A61K 31/495; A61K 31/496; A61K 31/5377; A61K 31/31; A61K 31/541; A61K 31/675; A61K 45/06; C07D 401/12; C07D 401/14; C07D 405/14; C07D 409/14; C07D 417/14; C07D 453/02; C07D 471/08; C07D 9/650958; C07D 9/65583

USPC .......... 514/255.05, 227.8, 235.8, 85; 544/405, 544/407, 120, 332, 58.4
See application file for complete search history.

(56) References Cited

U.S. PATENT DOCUMENTS 3,953,476 A       4/1976   Cragoe, Jr. et al.

FOREIGN PATENT DOCUMENTS

| GB | 1214408 A | 12/1970 |
|---|---|---|
| GB | 1214409 A | 12/1970 |
| WO | 2008135557 A1 | 11/2008 |
| WO | 2009138378 A1 | 11/2009 |
| WO | 2013003386 A1 | 1/2013 |
| WO | 2013003444 A1 | 1/2013 |

OTHER PUBLICATIONS

Sheridan "The Most Common Chemical Replacement s in Drug-Like Compounds" J. Chem. Inf. Comput. Sci., 2002, vol. 42, pp. 103-108.*
J. G. Cannon Chapter Nineteen in Burgers Medicinal Chemistry and Drug Discovery, Fifth Edition, vol. I: Principles and Practice, Wiley-Interscience 1995, pp. 783-802, 784.*
Berge, Stephen, M., et al; Review Article: Pharmaceutical Salts; Journal of Pharmaceutical Sciences (1977) vol. 66, No. 1 pp. 1-19.
European Search Report for EP 11187553 Date of Completion of the Search Feb. 10, 2012.
European Search Report for EP 11187566 Date of Completion of the Search May 10, 2012.

(Continued)

*Primary Examiner* — Kendra D Carter
(74) *Attorney, Agent, or Firm* — Michael P. Morris; Edward S. Lazer

(57) ABSTRACT

The present invention relates to compounds of general formula (I)

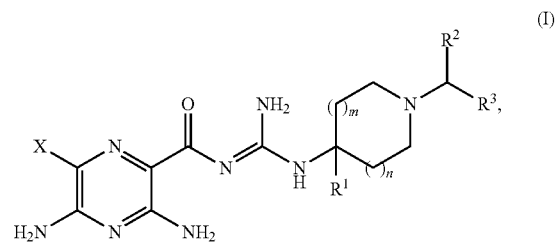

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

8 Claims, No Drawings

(56) References Cited

OTHER PUBLICATIONS

Hirsch, Andrew, J., et al; Design, Synthesis, and Structure-Activity relationships of Novel 2-Substituted Pyrazinoylguanidine Epithlial Sodium Channel Blockers: Drugs for Cystic Fibrosis and Chronic Brochitis; Journal of Medicinal Chemistry (2006) vol. 49, No. 14 pp. 4098-4115.

Li, Jack, H., et al; Stereoselective Blockade of Amphibian Epithelial Sodium Channels by Amiloride Analogs; The Journal of Pharmacology and Experimental Therapeutics (1993) vol. 267, No. 3 pp. 1081-1084.

Rogister, Francoise, et al; Novel Inhibitors of the Sodium-Calcium Exchanger: Benzene Ring Analogues of N-Guanidino Substituted Amiloride Derivatives; European Journal of Medicinal Chemistry (2001) vol. 36, No. 7-8 pp. 597-614.

Shepard, Kenneth, L. et al; 3,5-Diamino-6-Chloropyrazinecarboxylic Acid "Active Esters" and Their Reactions (1); Tetrahedron Letters (1969) vol. 54 pp. 4757-4760.

Short, James, H. et al., Sympathetic Nervous System Blocking Agents. Derivates of Guanidine and Related Compounds; Journal of Medicinal Chemistry (1963) vol. 6 pp. 275-283.

U.S. Appl. No. 13/662,791, filed Oct. 29, 2012, InventorArmin Heckel.

U.S. Appl. No. 13/662,792, filed Oct. 29, 2012, Inventor Joerg Kley.

European Search Report for EP 11194687 Date of Completion of the Search Mar. 7, 2012.

Laeckmann, D. et al., "Synthesis and Biological Evaluation of Aroylguanidines Related to Amilorade as Inhibitors of the Human Platelet Na+/H+Exchanger". Bioorganic Medical Chemistry 2002, 1793-1804.

Shepard, K.L., et al., Activated Esters of Substituted Pyrazinecarboxylic Acids (1). Journal of Heterocyclic Chemistry, 1976, 1219-1224.

Woodman, D.J., "N-t-Butyl-acyloxycrotonamides". Journal of Organic Chemistry, 1970, p. 83-87.

Alberola, A., et al., "The Reactions of 3-Unsubstituted Isoxazolium Salts with 1,2-Dinucleophiles, Synthesis of 4-Funtionalized 3-Aminoisoxazoles and 3-Aminopyrazoles". Synthesis 1988, 203-207.

International Search Report, Form PCT/ISR/210, for corresponding application PCT/EP2012/076101 date of mailing Jan. 22, 2013.

\* cited by examiner

TERTIARY AMINES, MEDICAMENTS CONTAINING SAID AMINES, USE THEREOF AND PROCESSES FOR THE PREPARATION THEREOF

1. FIELD OF THE INVENTION

The present invention relates to compounds of general formula (I)

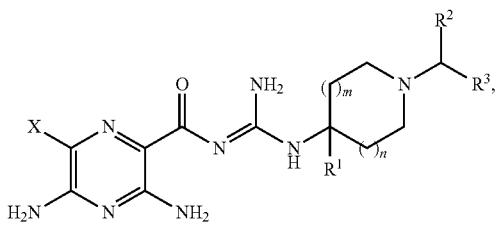

(I)

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2. BACKGROUND TO THE INVENTION

Amiloride type compounds are known from the prior art as active substances for example for the treatment of diseases of the lungs and airways (*J. Med. Chem.* 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

3. DETAILED DESCRIPTION OF THE INVENTION

It has surprisingly been found that the the problem mentioned above is solved by compounds of formula (I) of the present invention,

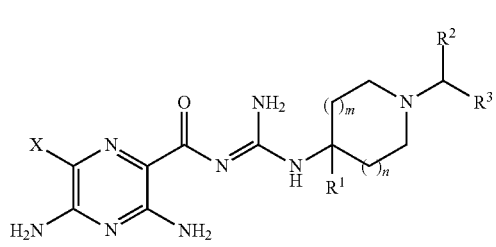

(I)

wherein
X denotes Cl or Br,
$R^1$ denotes H or methyl,
m, n independently from each other with the proviso that (m+n)<4, denote 0, 1 or 2,
$R^2$ denotes H or is selected from the group consisting of methyl, —C(O)O$R^{2.1}$ and —C(O)N$R^{2.2}R^{2.3}$, wherein
$R^{2.1}$ denotes H or is selected from the group consisting of optionally substituted $C_{1-8}$-alkyl-, optionally substituted $C_{3-8}$-cycloalkyl- and optionally substituted phenyl-$C_{1-4}$-alkyl-,
$R^{2.2}$, $R^{2.3}$ independently from each other denote H or are selected from the group consisting of optionally substituted $C_{1-8}$-alkyl-, optionally substituted $C_{3-8}$-cycloalkyl-, and optionally substituted —$C_{1-4}$-alkyl-$C_{6-10}$-aryl,
$R^3$ denotes H or is selected from the group consisting of
—CN, —$C_{3-4}$-alkyl-$C_{6-10}$-aryl, —$C_{1-4}$-alkyl-nonaromatic heterocycle, —$CH_2$—O—($C_2H_4$—O)$_q$—$CH_3$, —$CH_2$—O—($C_2H_4$—O)$_t$—H, —PO(O$R^{3.4}$)(O—$R^{3.5}$), —$C_{1-4}$-alkyl-S(O)$_2$OH, —$C_{1-4}$-alkyl-S(O)$_r$—$C_{1-6}$-alkyl, —$C_{1-4}$-alkyl-COOH, —$C_{1-4}$-alkyl-C(O)O$R^{3.8}$,
$C_{1-8}$-alkyl, optionally substituted $C_{3-8}$-cycloalkyl-, $R^{3.1}$—OC(O)—, $R^{3.2}$N($R^{3.3}$)C(O)—, optionally substituted C-linked nonaromatic heterocycle-$C_{1-3}$-alkyl, and —$(CH_2)_p$—N$R^{3.6}R^{3.7}$,
wherein,
p is 1, 2, 3 or 4,
q is 1, 2, 3 or 4,
r is 0, 1 or 2,
t is 1, 2, 3 or 4,
$R^{3.1}$ is selected from the group consisting of H, optionally substituted $C_{1-8}$-alkyl-, optionally substituted $C_{3-8}$-cycloalkyl-, hydroxyethoxy-$C_{2-4}$-alkyl-, methoxyethoxy-$C_{2-4}$-alkyl-, —$C_{1-4}$-alkyl-S(O)$_s$—$C_{1-4}$-alkyl, optionally substituted phenyl-$C_{1-2}$-alkyl-, optionally substituted heteroaryl-$C_{1-2}$-alkyl-, C-linked -5-7-membered nonaromatic heterocycle (mono- or bicyclic) and 5-7-membered nonaromatic heterocycle-$C_{1-4}$-alkyl-,
$R^{3.2}$, $R^{3.3}$ independently from each other denote H or are selected from the group consisting of optionally substituted $C_{1-8}$-alkyl-, optionally substituted $C_{3-8}$-cycloalkyl-, —$C_{2-8}$-alkyl-O—$C_{1-4}$-alkyl, hydroxy-$C_{2-4}$-alkyl-, methoxyethoxy-$C_{2-4}$-alkyl-, —$C_{1-8}$-alkyl-S(O)$_s$—$C_{1-6}$-alkyl, —$CH_2$—COOH, —$CH_2$—COO—$C_{1-4}$-alkyl, —$CH_2$—CO—NH—$C_{1-4}$-alkyl, —$C_{1-4}$-alkyl-5- to 7-membered nonaromatic heterocycle-$R^{3.3.3}$, —$C_{1-4}$-alkyl-5-to 7-membered heteroaryl-$R^{3.3.4}$, 5- to 8-membered nonaromatic heterocycle-$R^{3.3.5}$, -5-to 7-membered heteroaryl-$R^{3.3.6}$,
optionally substituted —$C_{1-4}$-alkyl-phenyl-$R^{3.3.1}$ and optionally substituted-phenyl-$R^{3.3.2}$,
wherein
s is 0, 1 or 2
$R^{3.3.1}$ denotes H or is selected from the group consisting of
—COOH, —COO—$C_{1-4}$-alkyl, —O—$C_{1-4}$-alkyl, —S—$CF_3$, —$SO_2$—$C_{1-3}$-alkyl, —$SO_2$—$NH_2$, —$CONH_2$, optionally substituted 5-to 7-membered nonaromatic heterocycle and -5-to 7-membered nonaromatic heterocycle-$C_{1-3}$-alkyl,
$R^{3.3.2}$ denotes H or is selected from the group consisting of
—CO—N($C_{1-3}$-alkyl)nonaromatic heterocycle-$C_{1-4}$-alkyl, —N($SO_2$—$C_{1-3}$-alkyl)($CH_2CONH$—$C_{1-3}$-alkyl), —N(CO$C_{1-3}$-alkyl)($C_{1-4}$-alkyl-N($C_{1-3}$-alkyl)$_2$), —N($C_{1-3}$-alkyl)CO—$C_{1-4}$-alkyl-N($C_{1-3}$-alkyl)$_2$, —$C_{1-3}$-nonaromatic heterocycle, —$SO_2$—N($C_{1-3}$-alkyl)$C_{1-3}$-alkyl-N($C_{1-3}$-alkyl)$_2$,
—$SO_2NH_2$, —$SO_2OH$, —COOH, —COO—$C_{1-3}$-alkyl, —$CONH_2$, —CONH—$C_{1-4}$-alkyl-N($C_{1-3}$-alkyl)$_2$, —O—$C_{2-3}$-alkyl-N($C_{1-3}$-alkyl)$_2$, —N(SO$_2$CH$_3$)—C$_{1-3}$-alkyl-N(C$_{1-3}$-alkyl)$_2$, and —C$_{2-3}$-alkyl-N(R$^{3.3.2.1}$)R$^{3.3.2.2}$, wherein, R$^{3.3.2.1}$ denotes H, C$_{1-4}$-alkyl-, C$_{1-4}$-alkyl-CO— or C$_{1-4}$-alkyl-SO$_2$—, R$^{3.3.2.2}$ denotes H or C$_{1-4}$-alkyl-, or R$^{3.3.2.3}$ and R$^{3.3.2.2}$ together with the nitrogen atom they are attached to form an optionally substituted 4-7-membered heterocycle containing at least one N-atom, R$^{3.3.3}$ denotes H or C$_{1-3}$-alkyl, R$^{3.3.4}$ denotes H or C$_{1-3}$-alkyl, R$^{3.3.5}$ denotes H, C$_{1-3}$-alkyl, oxo or —C$_{1-3}$-alkyl-COO—C$_{1-3}$-alkyl, R$^{3.3.6}$ denotes H, C$_{1-3}$-alkyl, oxo or —C$_{1-3}$-alkyl-COO—C$_{1-3}$-alkyl, R$^{3.2}$ and R$^{3.3}$ together with the nitrogen atom they are attached to form an optionally substituted 5- to 7-membered heterocycle, R$^{3.4}$, R$^{3.5}$ independently from each other denote H or C$_{1-4}$-alkyl, R$^{3.6}$ denotes H, C$_{1-4}$-alkyl-, C$_{1-4}$-alkyl-CO— or C$_{1-4}$-alkyl-SO$_2$—, R$^{3.7}$ denotes H or C$_{1-4}$-alkyl-, or R$^{3.6}$ and R$^{3.7}$ together with the nitrogen atom they are attached to form an optionally substituted 4-7-membered heterocycle containing at least one N-atom, R$^{3.8}$ denotes H or is selected from the group consisting of optionally substituted C$_{1-8}$-alkyl-, optionally substituted C$_{3-8}$-cycloalkyl- and optionally substituted phenyl-C$_{1-4}$-alkyl-, and the tautomers, optionally the hydrates, optionally the solvates and optionally the pharmaceutically acceptable acid addition salts thereof.

Preferred compounds of formula (I) are those, wherein

X denotes Cl or Br,

R$^1$ denotes H, m, n independently from each other with the proviso that (m+n)<4, denote 0, 1 or 2, R$^2$ denotes H or is selected from the group consisting of methyl, —C(O)OR$^{21}$ and —C(O)NR$^{2.2}$R$^{2.3}$, wherein R$^{2.1}$ denotes C$_{1-3}$-alkyl-, R$^{2.2}$, R$^{2.3}$ independently from each other denote H or phenyl-C$_{1-4}$-alkyl-, R$^3$ is selected from the group consisting of —CN, —CH$_2$-morpholinyl, —CH$_2$—O—(C$_2$H$_4$—O)$_3$—CH$_3$, —PO(O—R$^{3.4}$)(O—R$^{3.5}$), —C$_{1-3}$-alkyl-S(O)$_2$OH, —C$_{1-4}$-alkyl-S(O)$_r$—C$_{1-6}$-alkyl, preferably —CH$_2$—S—C$_{1-3}$-alkyl, C$_{1-3}$-alkyl, —C$_{1-3}$-alkyl-COOH, —C$_{1-3}$-alkyl-COOCH$_3$, C$_{3-8}$-cycloalkyl-, R$^{3.1}$—OC(O)—, R$^{3.2}$N(R$^{3.3}$)C(O)—, and —C-linked non-aromatic heterocycle-R$^{3.3.6}$, wherein r is 0, 1 or 2, R$^{3.1}$ denotes H, C$_{1-8}$-alkyl-, or phenyl-C$_{1-2}$-alkyl-, R$^{3.2}$, R$^{3.3}$ independently from each other denote H or are selected from the group consisting of C$_{1-8}$-alkyl-, —C$_{1-8}$-alkyl-O—C$_{1-4}$-alkyl, —C$_{1-8}$-alkyl-S—C$_{1-4}$-alkyl, —C$_{1-4}$-alkyl-S(O)$_s$—C$_{2-6}$-alkyl, —CH$_2$—COOH, —CH$_2$—COO—C$_{1-4}$-alkyl, —CH$_2$—CO—NH—C$_{1-4}$-alkyl, optionally substituted —CH$_2$-phenyl-R$^{3.3.1}$, optionally substituted-phenyl-R$^{3.3.2}$, —C$_{1-4}$-alkyl-5- to 7-membered nonaromatic heterocycle-R$^{3.3.3}$, —C$_{1-4}$-alkyl-5-to 7-membered heteroaryl-R$^{3.3.4}$, -5-to 8-membered nonaromatic heterocycle-R$^{3.3.5}$ and -5-to 7-membered heteroaryl-R$^{3.3.6}$, wherein s is 0, 1 or 2

R$^{3.3.1}$ denotes H or is selected from the group consisting of

—SO$_2$—C$_{1-3}$-alkyl, —SO$_2$—NH$_2$, —CONH$_2$, -5-to 7-membered nonaromatic heterocycle-R$^{3.3.7}$, —OMe, —S—CF$_3$ and —COO—C$_{1-4}$-alkyl, R$^{3.3.2}$ denotes H or is selected from the group consisting of —CO—N(CH$_3$)(nonaromatic heterocycle-C$_{1-4}$-alkyl), —N(SO$_2$—CH$_3$)(CH$_2$CONHCH$_3$), —N(COCH$_3$)(C$_{1-4}$-alkyl-N(CH$_3$)$_2$), —N(CH$_3$)COC$_{1-4}$-alkyl-N(CH$_3$)$_2$, —C$_{1-3}$-alkyl-nonaromatic heterocycle, —SO$_2$—N(CH$_3$)(C$_{1-3}$-alkyl-N(CH$_3$)$_2$), —SO$_2$NH$_2$, —SO$_2$OH, COOH, —COO—C$_{1-3}$-alkyl, —CONH$_2$, —CONH—C$_{1-3}$-alkyl-N(CH$_3$)$_2$, —O—C$_{1-3}$-alkyl-N(CH$_3$)$_2$ and —N(SO$_2$CH$_3$)(C$_{1-3}$-alkyl-N(CH$_3$)$_2$), R$^{3.3.3}$ denotes H or methyl, R$^{3.3.4}$ denotes H or methyl, R$^{3.3.5}$ denotes H, C$_{1-3}$-alkyl or oxo, R$^{3.3.6}$ denotes H, oxo, CH$_3$ or —CH$_2$—COO—CH$_3$ R$_{3.3.7}$ denotes H, C$_{1-3}$-alkyl or oxo, or R$^{3.2}$ and R$^{3.3}$ together with the nitrogen atom they are attached to form an optionally substituted 5- to 7-membered heterocycle, R$^{3.4}$, R$^{3.5}$ independently from each other denote H or C$_{1-4}$-alkyl.

Particularly preferred are compounds of formula (I), wherein

X denotes Cl,

R$^1$ denotes H, m, n independently from each other with the proviso that 0<(m+n)<4, denote 0, 1 or 2, and R$^2$ denotes H.

Also particularly preferred are compounds of formula (I), wherein

R$^2$ denotes H,

R$^3$ is selected from the group consisting of

—CN, —CH$_2$-morpholinyl, —PO(O—R$^{3.4}$)(O—R$^{3.5}$), —C$_{1-3}$-alkyl-S(O)$_2$OH, —C$_{1-4}$-alkyl-S(O)$_r$—C$_{1-6}$-alkyl, —C$_{1-3}$-alkyl-COOH, —C$_{1-3}$-alkyl-COOCH$_3$ and —CH$_2$—COO—C$_{1-3}$-alkyl, wherein R$^{3.4}$, R$^{3.5}$ independently from each other denote H or C$_{1-4}$-alkyl.

Also particularly preferred are compounds of formula (I), wherein

R$^2$ denotes H,

R$^3$ is selected from the group consisting of

R$^{3.1}$—OC(O)—, R$^{3.2}$N(R$^{3.3}$)C(O)—, —C$_{1-3}$-alkyl-COOH, —C$_{1-3}$-alkyl-COOCH$_3$ and —CH$_2$—COO—C$_{1-3}$-alkyl wherein R$^{3.1}$ denotes H, C$_{1-4}$-alkyl or phenyl-C$_{1-2}$-alkyl-, R$^{3.2}$ denotes H, methyl, ethyl or methoxyethyl, and R$^{3.3}$ is selected from the group consisting of optionally substituted C$_{1-8}$-alkyl-optionally substituted C$_{3-8}$-cycloalkyl-, —C$_{2-8}$-alkyl-O—C$_{1-4}$-alkyl, hydroxy-C$_{2-4}$-alkyl-, —C$_{1-4}$-alkyl-phenyl-R$^{3.3.1}$ and —C$_{1-4}$-alkyl-5- to 7-membered heteroaryl-R$^{3.3.4}$, wherein R$^{3.3.1}$ and R$^{3.3.4}$ denote H.

Also particularly preferred are compounds of formula (I), wherein
$R^2$ denotes H,
$R^3$ denotes $R^{3.2}N(R^{3.3})C(O)$—,
  wherein
    $R^{3.2}$ denotes H or methyl,
    $R^{3.3}$ denotes optionally substituted $CH_2$-phenyl-$R^{3.3.1}$, optionally substituted-phenyl-$R^{3.3.2}$, —$C_{1-4}$-alkyl-5-to 7-membered heteroaryl-$R^{3.3.4}$ or -5- to 7-membered heteroaryl-$R^{3.3.6}$ wherein
      $R^{3.3.1}$ denotes H or is selected from the group consisting of
        —$SO_2$—$C_{1-3}$-alkyl, —$SO_2$—$NH_2$, —$CONH_2$ and -5- to 7-membered nonaromatic heterocycle-$C_{1-3}$-alkyl,
      $R^{3.3.2}$ denotes H or is selected from the group consisting of
        —CO—$N(CH_3)$(nonaromatic heterocycle-$C_{1-4}$-alkyl), —$N(SO_2$—$CH_3)(CH_2CONHCH_3)$, —$N(COCH_3)(C_{1-4}$-alkyl-$N(CH_3)_2)$, —$N(CH_3)COC_{1-4}$-alkyl-$N(CH_3)_2$, —$C_{1-3}$-nonaromatic heterocycle, —$SO_2$—$N(CH_3)(C_{1-3}$-alkyl-$N(CH_3)_2)$, —$SO_2NH_2$, —$SO_2OH$,
        COOH, —COO—$C_{1-3}$alkyl, —$CONH_2$, —CONH—$C_{1-3}$-alkyl-$N(CH_3)_2$, —O—$C_{1-3}$-alkyl-$N(CH_3)_2$ and —$N(SO_2CH_3)(C_{1-3}$-alkyl-$N(CH_3)_2)$,
      $R^{3.3.4}$ denotes H or methyl, and
      $R^{3.3.6}$ denotes H or methyl.

A further embodiment of the current invention are compounds of formula (I) or a pharmaceutically acceptable salt thereof as a medicament.

A further embodiment of the current invention are compounds of formula (I) or a pharmaceutically acceptable salt thereof for the treatment of a disease selected from among respiratory diseases or complaints and allergic diseases of the airways.

Preferred are compounds of formula (I) or a pharmaceutically acceptable salt thereof for the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins.

A further embodiment of the current invention is a pharmaceutical composition comprising at least one compound according to the invention or a pharmaceutically acceptable salt thereof and a pharmaceutically acceptable carrier.

A further embodiment of the current invention are medicament combinations which contain, besides one or more compounds of a compound according to anyone of claims 1 to 6, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

4. USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. (also see Pharmaceutical salts, Birge, S. M. et al., J. Pharm. Sci., (1977), 66, 1-19). As the compounds of the present invention may have both, acid as well as basic groups, those compounds may therefore be present as internal salts too.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

The parent compound can generally be obtained from its salt by sufficiently altering the pH in solution using an appropriate base or acid, so that the pH is 3 units above the pKa of the parent base and for an acid the pH is 3 units below the pKa of the parent acid.

Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

The term "aryl" as used herein, either alone or in combination with another substituent, means either an aromatic monocyclic system or aromatic multicyclic systems containing carbon atoms. For example, aryl includes a phenyl or a naphthyl ring system, wherein aryl means generally an aromatic system, for example phenyl.

The term "heterocycle" or "heterocyclic rings" as used herein, either alone or in combination with another substituent, means a monovalent substituent derived by removal of a hydrogen from a five-, six- or seven-membered saturated or unsaturated (including aromatic) heterocycle containing carbon atoms and one, two, three or four ring heteroatoms selected from nitrogen, oxygen and sulfur. Examples of suitable heterocycles include: tetrahydrofuran, thiophene, diazepine, isoxazole, piperidine, dioxane, morpholine, piperazine or

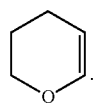

By the term "non aromatic heterocycle" are meant five-, six- or seven-membered, saturated or unsaturated heterocyclic rings or 5-10 membered, bicyclic hetero rings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

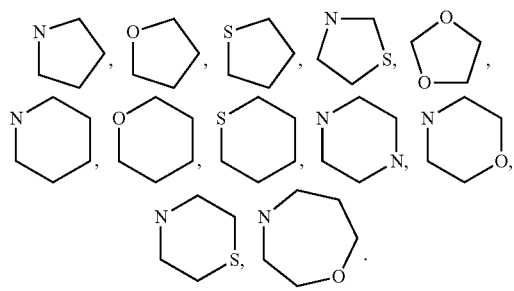

Unless stated otherwise, a heterocyclic ring may be provided with a keto group. Examples include:

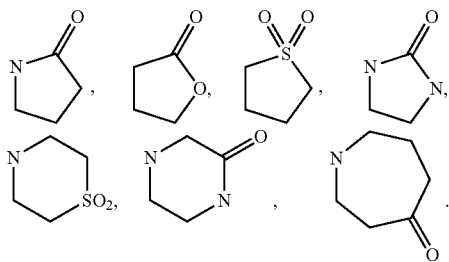

Examples of 5-10-membered bicyclic heterocyclic rings are pyrrolizine, indole, indolizine, isoindole, indazole, purine, quinoline, isoquinoline, benzimidazole, benzofurane, benzopyrane, benzothiazole, benzoisothiazole, pyridopyrimidine, pteridine, pyrimidopyrimidine,

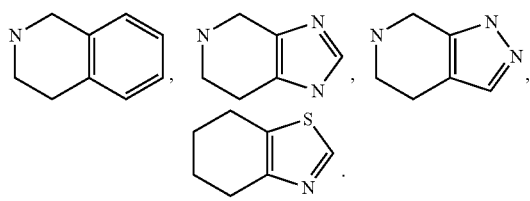

Although the term heterocyclic rings includes heterocyclic aromatic groups, the term heterocyclic aromatic groups ("heteroaryl") denotes five- or six-membered heterocyclic aromatic groups or 5-10 membered, bicyclic heteroaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

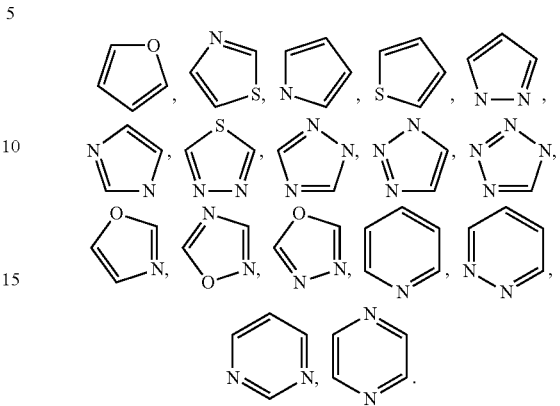

Examples of 5-10-membered bicyclic heteroaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine, pyrimidopyrimidine.

The term "halogen" as used herein means a halogen substituent selected from fluoro, chloro, bromo or iodo.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and isopropyl, butyl includes iso-butyl, sec-butyl and tert-butyl etc.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

The term "$C_{3-8}$-cycloalkyl" (including those which are part of other groups) as used herein means cyclic alkyl groups with 3 to 8 carbon atoms, preferred are cyclic alkyl groups with 5 to 6 carbon atoms. Examples include: cyclopropyl, cyclobutyl, cyclopentyl, cyclohexyl, cycloheptyl or cyclooctyl.

By the term "$C_{3-6}$-cycloalkenyl" (including those which are part of other groups) is a cyclic alkyl group meant with 5 or 6 carbon atoms which contain one or two double bonds. Examples include: cyclopentenyl, cyclopentadienyl, cyclohexenyl or cyclohexadienyl.

In all cases of contradictions between structure and their naming structure shall prevail.

5. PREFERRED EMBODIMENTS

The symbol X denotes Cl or Br, preferably Cl.
The substituent $R^1$ denotes H or methyl, preferably H.
The variable m with the proviso that (m+n)<4, denotes 0, 1 or 2, preferably 0 or 1, particularly preferred 1.
The variables n with the proviso that (m+n)<4, denotes 0, 1 or 2, preferably 0 or 1, particularly preferred 1.
The substituent $R^2$ denotes H or is selected from the group consisting of
  methyl, —C(O)OR$^{2.1}$ and —C(O)NR$^{2.2}$R$^{2.3}$, preferably H
The substituent $R^{2.1}$ denotes H or is selected from the group consisting of
  optionally substituted $C_{1-8}$-alkyl-, preferably unsubstituted $C_{1-8}$-alkyl- or $C_{1-8}$-alkyl-substituted by up to two substituents selected from the group consisting of HO—, NH$_2$—, CN—, $C_{1-4}$-alkoxy and ethyl, particularly preferred $C_{1-8}$-alkyl-substituted by ethyl,
  optionally substituted $C_{3-8}$-cycloalkyl-, preferably substituted by up to two substituents selected from the group consisting of HO—, NH$_2$—, CN— and $C_{1-4}$-alkoxy,
  and optionally substituted phenyl-$C_{1-4}$-alkyl-.
Preferably $R^{2.1}$ denotes H or $C_{1-3}$-alkyl-, preferably ethyl.
The substituent $R^{2.2}$ denotes H or is selected from the group consisting of
  optionally substituted $C_{1-8}$-alkyl-, preferably unsubstituted $C_{1-8}$-alkyl- or substituted by up to two substituents selected from the group consisting of HO—, NH$_2$—, CN— and $C_{1-4}$-alkoxy, particular preferred unsubstituted $C_{1-8}$-alkyl-,
  optionally substituted $C_{3-8}$-cycloalkyl-, preferably unsubstituted $C_{3-8}$-cycloalkyl- or substituted by up to two substituents selected from the group consisting of HO—, NH$_2$—, CN— and $C_{1-4}$-alkoxy, particular preferred unsubstituted $C_{3-8}$-cycloalkyl-, and
  optionally substituted $C_{6-10}$-aryl-$C_{1-4}$-alkyl-, preferably phenyl-ethyl-.
The substituent $R^{2.3}$ denotes H or is selected from the group consisting of
  optionally substituted $C_{1-8}$-alkyl-, preferably unsubstituted $C_{1-8}$-alkyl- or substituted by up to two substituents selected from the group consisting of HO—, NH$_2$—, CN— and $C_{1-4}$-alkoxy, particular preferred unsubstituted $C_{1-8}$-alkyl-,
  optionally substituted $C_{3-8}$-cycloalkyl-, preferably substituted by up to two substituents selected from the group consisting of HO—, NH$_2$—, CN— and $C_{1-4}$-alkoxy, particular preferred unsubstituted $C_{3-8}$-cycloalkyl-, and
  optionally substituted $C_{6-10}$-aryl-$C_{1-4}$-alkyl-, preferably phenyl-ethyl-.

Preferably $R^{2.2}$, $R^{2.3}$ independently from each other denote H or phenyl-$C_{1-4}$-alkyl-, preferably H or phenyl-ethyl-.
The substituent $R^3$ denotes H or is selected from the group consisting of
  —CN, —C$_{3-4}$-alkyl-C$_{6-10}$-aryl, preferably —C$_{3-4}$-alkyl-phenyl, —C$_{1-4}$-alkyl-non aromatic heterocycle, preferably —C$_{1-2}$-alkyl-1-morpholine, —CH$_2$—O—(C$_2$H$_4$—O)$_q$—CH$_3$, preferably —CH$_2$—O—C$_2$H$_4$—O—CH$_3$,
  —CH$_2$—O—(C$_2$H$_4$—O)$_t$—H, preferably —CH$_2$—O—C$_2$H$_4$—OH, —PO(O—R$^{3.4}$)(O—R$^{3.5}$), preferably —PO(O—C$_2$H$_5$)$_2$, —C$_{1-4}$-alkyl-S(O)$_2$OH, preferably —CH$_2$—S(O)$_2$—C$_2$H$_5$, C$_{1-4}$-alkyl-COOH, preferably CH$_2$—COOH, —C$_{1-4}$-alkyl-C(O)OR$^{3.8}$, preferably —CH$_2$—C(O)OR$^{3.8}$,
  optionally substituted $C_{1-8}$-alkyl, preferably unsubstituted $C_{1-8}$-alkyl or $C_{1-8}$-alkyl substituted by up to two substituents selected from the group consisting of HO—, NH$_2$—, CN— and $C_{1-4}$-alkoxy-, particularly preferred methyl,
  optionally substituted $C_{3-8}$-cycloalkyl-, preferably unsubstituted $C_{3-8}$-cycloalkyl- or $C_{3-8}$-cycloalkyl-substituted by up to two substituents selected from the group consisting of HO—, NH$_2$—, CN— and $C_{1-4}$-alkoxy-, particularly preferred cyclopentyl,
  R$^{3.1}$—OC(O)—, R$^{3.2}$N(R$^{3.3}$)C(O)—, optionally substituted —C-linked-nonaromatic heterocycle-C$_{1-3}$-alkyl, preferably piperidinyl-CH$_3$ and —(CH$_2$)$_p$—NR$^{3.6}$R$^{3.7}$.
Preferably $R^3$ is selected from the group consisting of
  —CN, —CH$_2$-morpholinyl, —CH$_2$—O—(C$_2$H$_4$—O)$_3$—CH$_3$, —PO(O—R$^{3.4}$)(O—R$^{3.5}$), —CH$_2$—S—C$_{1-3}$-alkyl, —C$_{1-3}$-alkyl-S(O)$_2$OH, —C$_{1-4}$-alkyl-S(O)$_r$—C$_{1-8}$-alkyl, C$_{1-3}$-alkyl, —C$_{1-3}$-alkyl-COOH, —C$_{1-3}$-alkyl-COOCH$_3$, $C_{3-8}$-cycloalkyl-, R$^{3.1}$—OC(O)—, R$^{3.2}$N(R$^{3.3}$)C(O)— and —C-linked nonaromatic heterocycle-R$^{3.3.6}$.
The variable p is 1, 2, 3 or 4, preferably 1.
The variable q is 1, 2, 3 or 4, preferably q=1.
The variable r is 0, 1 or 2, preferably 2.
The variable t is 1, 2, 3 or 4, preferably 1.
The substituent $R^{3.1}$ is selected from the group consisting of H, optionally substituted $C_{1-8}$-alkyl-, preferably methyl, ethyl, or butyl, optionally substituted $C_{3-8}$-cycloalkyl-, preferably unsubstituted $C_{3-8}$-cycloalkyl- or $C_{3-8}$-cycloalkyl-substituted by up to two substituents selected from the group consisting of HO—, NH$_2$—, CN— and $C_{1-4}$-alkoxy-, hydroxyethoxy-$C_{1-4}$-alkyl-, preferably hydroxyethoxyethyl-, methoxyethoxy-$C_{1-4}$-alkyl-, preferably methoxyethoxyethyl-, —C$_{1-4}$-alkyl-S(O)$_s$—C$_{1-4}$-alkyl, optionally substituted phenyl-$C_{1-2}$-alkyl-, preferably phenyl-CH$_2$—, optionally substituted heteroaryl-$C_{1-2}$-alkyl-, preferably 1-morpholinylmethyl- or 1-piperidinylmethyl-, C-linked 5-7-membered nonaromatic nonaromatic heterocycle (mono- or bicyclic), preferably tetrahydrofuranyl and 5-7-membered nonaromatic heterocycle-$C_{1-4}$-alkyl-, preferably tetrahydrofuranylmethyl-.
Preferably $R^{3.1}$ denotes H, $C_{1-8}$-alkyl- or phenyl-$C_{1-2}$-alkyl-.
The substituent $R^{3.2}$ denotes H or is selected from the group consisting of optionally substituted $C_{1-8}$-alkyl-, preferably unsubstituted $C_{1-2}$-alkyl, optionally substituted $C_{3-8}$-cycloalkyl-, preferably unsubstituted $C_{3-8}$-cycloalkyl- or $C_{3-8}$-cycloalkyl-substituted by up to two substituents selected from the group consisting of HO—, NH$_2$—, CN— and $C_{1-4}$-alkoxy-, —C$_{1-8}$-alkyl-O—C$_{1-4}$-alkyl, preferably methoxyethyl-, hydroxy-$C_{1-4}$-alkyl-, preferably hydroxyethyl-, methoxyethoxy-$C_{1-4}$-alkyl-, preferably methoxyethoxyethyl-, $—C_{1-8}$-alkyl-S(O)$_s$—$C_{1-6}$-alkyl, —$CH_2$—COOH, —$CH_2$—COO—$C_{1-4}$-alkyl, preferably —$CH_2$—COO—$CH_3$, —$CH_2$—CO—NH—$C_{1-4}$-alkyl, preferably —$CH_2$—CO—NH-methyl or $CH_2$—CO—NH-ethyl, —$C_{1-4}$-alkyl-5-to 7-membered nonaromatic heterocycle-$R^{3.3.3}$, preferably 1-morpholinyl-ethyl-, —$C_{1-4}$-alkyl-5-to 7-membered heteroaryl-$R^{3.3.4}$, preferably -pyrazolyl-$R^{3.3.4}$, -furanyl-$R^{3.3.4}$ or -thiophenyl-$R^{3.3.4}$, -5- to 8-membered nonaromatic heterocycle-$R^{3.3.5}$, preferably tetrahydro-thiopyranyl-$R^{3.3.5}$ or tetrahydro-pyranyl-$R^{3.3.5}$, 5-to 7-membered heteroaryl-$R^{3.3.6}$, preferably pyridin-$R^{3.3.6}$, optionally substituted —$C_{1-4}$-alkyl-phenyl-$R^{3.3.1}$, preferably unsubstituted —$C_{1-4}$-alkyl-phenyl-$R^{3.3.1}$ or —$C_{1-4}$-alkyl-phenyl-$R^{3.3.1}$, wherein the phenylene moiety may be optionally substituted by up to two substituents selected from the group consisting of F, Cl, OH, OMe and $CH_3$, particularly preferred $CH_2$-phenyl-$R^{3.3.1}$, and optionally substituted-phenyl-$R^{3.3.2}$, preferably unsubstituted-phenyl-$R^{3.3.2}$ or -phenyl-$R^{3.3.2}$, wherein the phenylene moiety may be optionally substituted by up to two substituents selected from the group consisting of F, Cl, OH, OMe and $CH_3$, Particularly preferred $R^{3.2}$ denotes H.

The substituent $R^{3.3}$ denotes H or is selected from the group consisting of optionally substituted $C_{1-8}$-alkyl-, preferably unsubstituted $C_{1-2}$-alkyl, optionally substituted $C_{3-8}$-cycloalkyl-, preferably unsubstituted $C_{3-8}$-cycloalkyl- or $C_{3-8}$-cycloalkyl-substituted by up to two substituents selected from the group consisting of HO—, $NH_2$—, CN— and $C_{1-4}$-alkoxy-, —$C_{1-8}$-alkyl-O—$C_{1-4}$-alkyl, preferably methoxyethyl-, hydroxy-$C_{1-4}$-alkyl-, preferably hydroxyethyl-, methoxyethoxy-$C_{1-4}$-alkyl-, preferably methoxyethyl-, —$C_{1-8}$-alkyl-S(O)$_s$—$C_{1-6}$-alkyl, —$CH_2$—COOH, —$CH_2$—COO—$C_{1-4}$-alkyl, preferably —$CH_2$—COO—$CH_3$, —$CH_2$—CO—NH—$C_{1-4}$-alkyl, preferably —$CH_2$—CO—NH—$CH_3$, —$C_{1-4}$-alkyl-5-to 7-membered nonaromatic heterocycle-$R^{3.3.3}$, preferably 1-morpholinyl-ethyl-, —$C_{1-4}$-alkyl-5-to 7-membered heteroaryl-$R^{3.3.4}$, preferably —$C_{1-4}$-alkyl-pyrazolyl, —$C_{1-4}$-alkyl-furanyl or —$C_{1-4}$-alkyl-thiophenyl, 5- to 8-membered nonaromatic heterocycle-$R^{3.3.3}$, preferably tetrahydro-thiopyranyl or tetrahydropyranyl, 5-to 7-membered heteroaryl-$R^{3.3.6}$ preferably -pyridinyl-$R^{3.3.6}$, optionally substituted —$C_{1-4}$-alkyl-phenyl-$R^{3.3.1}$, preferably unsubstituted —$C_{1-4}$-alkyl-phenyl-$R^{3.3.1}$ or —$C_{1-4}$-alkyl-phenyl-$R^{3.3.1}$, wherein the phenylene moiety may be optionally substituted by up to two substituents selected from the group consisting of F, Cl, OH, OMe and $CH_3$, particularly preferred —$CH_2$-phenyl-$R^{3.3.1}$, optionally substituted-phenyl-$R^{3.3.2}$, preferably unsubstituted-phenyl-$R^{3.3.2}$ or -phenyl-$R^{3.3.2}$, wherein the phenylene moiety may be optionally substituted by up to two substituents selected from the group consisting of F, Cl, OH, OMe and $CH_3$.

The variable s is 0, 1 or 2, preferably 2.

The substituent $R^{3.3.1}$ denotes H or is selected from the group consisting of
—COOH, —COO—$C_{1-4}$-alkyl, preferably —COOH, —O—$C_{1-4}$-alkyl, preferably —OMe, —S—$CF_3$ or —$SO_2$—$C_{1-3}$-alkyl, preferably —$SO_2$—$CH_3$, —$SO_2$—$NH_2$ or —$CONH_2$, optionally substituted 5-to 7-membered nonaromatic heterocycle-, preferably unsubstituted 5-to 7-membered nonaromatic heterocycle-, and -5-to 7-membered nonaromatic heterocycle-$C_{1-3}$-alkyl, preferably -piperazinyl-$CH_3$.

Preferably the substituent $R^{3.3.1}$ denotes H or is selected from the group consisting of
—$SO_2$—$C_{1-3}$-alkyl, —$SO_2$—$NH_2$, —$CONH_2$, -5- to 7-membered nonaromatic heterocycle-$R^{3.3.7}$, —O—$C_{1-4}$-alkyl, —S—$CF_3$ and —COO—$C_{1-4}$-alkyl.

The substituent $R^{3.3.2}$ denotes H or is selected from the group consisting of
—CO—N($C_{1-3}$-alkyl)nonaromatic heterocycle-$C_{1-4}$-alkyl, preferably —CO—N($CH_3$)-piperidinyl-$CH_3$, —N($SO_2$—$C_{1-3}$-alkyl)($CH_2$CONH $C_{1-3}$-alkyl), —N(COC$_{1-3}$-alkyl)($C_{1-4}$-alkyl-N($C_{1-3}$-alkyl)$_2$), —N($C_{1-3}$-alkyl)CO—$C_{1-4}$-alkyl-N($C_{1-3}$-alkyl)$_2$, —$C_{1-3}$-alkyl-nonaromatic heterocycle, preferably —$CH_2$-morpholinyl or —$CH_2$-piperidinyl, —$SO_2$—N($C_{1-3}$-alkyl)$C_{1-3}$-alkyl-N($C_{1-3}$-alkyl)$_2$, —$SO_2NH_2$, —$SO_2OH$, —COOH, —COO—$C_{1-3}$-alkyl, —$CONH_2$, —CONH—$C_{1-3}$-alkyl-N($C_{1-3}$-alkyl)$_2$, —O—$C_{2-3}$-alkyl-N($C_{1-3}$-alkyl)$_2$, —N($SO_2CH_3$)—$C_{1-3}$-alkyl-N($C_{1-3}$-alkyl)$_2$ and —$C_{1-3}$-alkyl-N($R^{3.3.2.1}$)$R^{3.3.2.2}$, preferably —$CH_2$—N($R^{3.3.2.1}$)$R^{3.3.2.2}$.

The substituent $R^{3.3.2.1}$ denotes H, $C_{1-4}$-alkyl-, $C_{1-4}$-alkyl-CO— or $C_{1-4}$-alkyl-$SO_2$—, preferably $C_{1-2}$-alkyl-.

The substituent $R^{3.3.2.2}$ denotes H or $C_{1-4}$-alkyl-, preferably $C_{1-2}$-alkyl-, or $R^{3.3.2.1}$ and $R^{3.3.2.2}$ together with the nitrogen atom they are attached to form an optionally substituted 4-7-membered heterocycle containing at least one N-atom, preferably morpholine or pyrrolidine.

The substituent $R^{3.3.3}$ denotes H or $C_{1-3}$-alkyl, preferably methyl.

The substituent $R^{3.3.4}$ denotes H or $C_{1-3}$-alkyl, preferably methyl.

The substituent $R^{3.3.5}$ denotes H, $C_{1-3}$-alkyl, oxo or —$C_{1-3}$-alkyl-COO—$C_{1-3}$-alkyl, preferably —$CH_2$—COO—$CH_3$ or $C_{1-3}$-alkyl.

The substituent $R^{3.3.6}$ denotes H, oxo, $CH_3$ or —$CH_2$—COO—$CH_3$.

The substituent $R^{3.3.7}$ H, $C_{1-3}$-alkyl or oxo.

$R^{3.2}$ and $R^{3.3}$ together with the nitrogen atom they are attached to may form an optionally substituted 5- to 7-membered heterocycle, preferably a 5- to 7-membered heterocycle substituted by oxo, preferably containing 0 to 1 additional heteroatoms, most preferably N or S.

Particularly preferred $R^{3.2}$ and $R^{3.3}$ together with the nitrogen atom they are attached form thiomorpholinyl, thiomorpholinyl-S-oxide; S,S-dioxo-thiomorpholinyl or morpholinyl.

$R^{3.4}$ denotes H or $C_{1-4}$-alkyl, preferably H, ethyl or methyl.

$R^{3.5}$ denotes H or $C_{1-4}$-alkyl, preferably H or ethyl.

$R^{3.6}$ denotes H, $C_{1-4}$-alkyl-, $C_{1-4}$-alkyl-CO— or $C_{1-4}$-alkyl-$SO_2$—, preferably H or methyl-CO— or methyl-$SO_2$—.

$R^{3.7}$ denotes H or $C_{1-4}$-alkyl-, preferably methyl or ethyl, $R^{3.6}$ and $R^{3.7}$ together with the nitrogen atom they are attached to form an optionally substituted 4-7-membered heterocycle containing at least one N-atom, $R^{3.8}$ denotes H or is selected from the group consisting of
optionally substituted $C_{1-8}$-alkyl-, preferably ethyl, optionally substituted $C_{3-8}$-cycloalkyl-, preferably unsubstituted $C_{5-6}$-cycloalkyl- or $C_{5-6}$-cycloalkyl-substituted by up to two substituents selected from the group consisting of HO—, $NH_2$—, CN— and $C_{1-4}$-alkoxy-, and optionally substituted phenyl-$C_{1-4}$-alkyl-, preferably substituted phenylmethyl-.

Any of the definitions of substituents and variables described above may be combined with each other.

6. PREPARATION

The following methods are suitable for preparing compounds of general formula (I), The compounds according to the invention may be obtained using methods of synthesis which are known to the one skilled in the art and described in the literature of organic synthesis. General methods for functional groups protection and deprotection steps are described e.g. in: Greene, T. W. and Wuts, P. G. M. (eds.): *Protective Groups in Organic Synthesis, third edition* 1999; John Wiley and Sons, inc. Preferably the compounds are obtained analogously to the methods of preparation explained more fully hereinafter, in particular as described in the experimental section.

Compounds of formula (II) can be prepared by reacting S-methylisothiourea (which may be generated in situ from its sulphuric acid salt by addition of base) with a compound of formula (IV) in a solvent like DCM, THF, TBME, water or a mixture of these solvents, preferably at r.t. Compounds (IV) can be prepared from a compound of formula (V) and a 2-tert-butyl-5-methyl-isoxazolium salt of general formula (VI), which can be applied as an isolated salt (e.g. the hexafluorophosphate salt; $X=PF_6$) or generated in situ from tert-butanol, 5-methylisoxazole and trifluoromethanesulphonic acid. The latter reaction is preferably performed in a solvent like DMF or in a solvent mixture with the addition of triethylamine or another base, preferably while cooling to 0-10° C.

Scheme 2

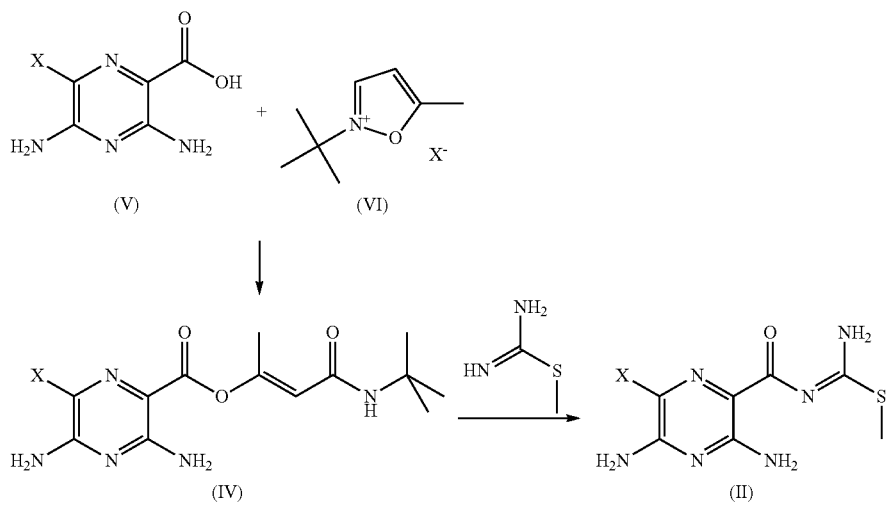

Compounds of general formula (I) can be prepared by reacting a compound of formula (II) with primary amines of formula (III) in a solvent like THF, acetonitrile or DMF or in a solvent mixture, preferably in the presence of a base, especially when the primary amine (III) is applied as an acid addition salt, preferably at r.t.

Scheme 1

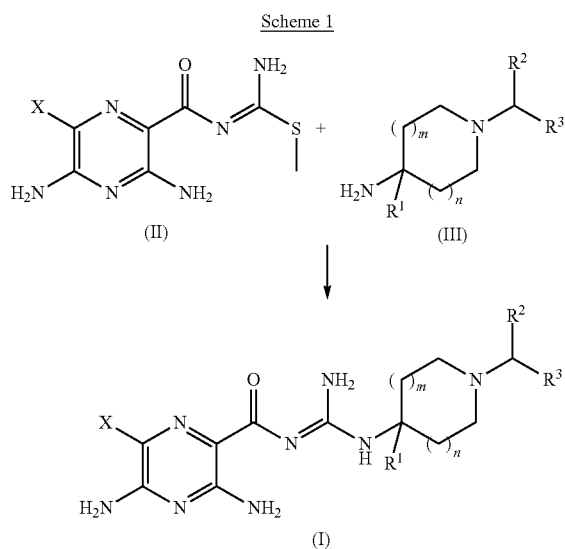

Compounds of general formula (III) can be prepared from compounds of general formula (VII) by removal of the respective protecting group, preferably the BOC(tert-Butoxycarbonyl) or FMOC (9H-Fluoren-9-yl-methoxycarbonyl) protecting group which can be removed by standard acidic or basic conditions, respectively. Compounds of general formula (VII) can be modified using methods of synthesis which are known to the one skilled in the art and described in the literature of organic synthesis, preferably by functional group protection or deprotection steps, esterifications, amidations, hydrogenations, or 1,3-dipolar cycloadditions of an azide to a terminal alkyne group or vice versa. Thereby, before such a modification, the structures of $R^2$ and $R^3$ may be beyond of what is claimed hereinafter. Compounds of general formula (VII) can be prepared from secondary amines of general formula (VIII), preferably either by alkylation with a compound of general formula (IX) (wherein the leaving group LG is preferably Cl, Br, OMesyl, or OTosyl), or by reductive amination with an aldehyde of general formula (X) (wherein $R^2=H$).

Scheme 3

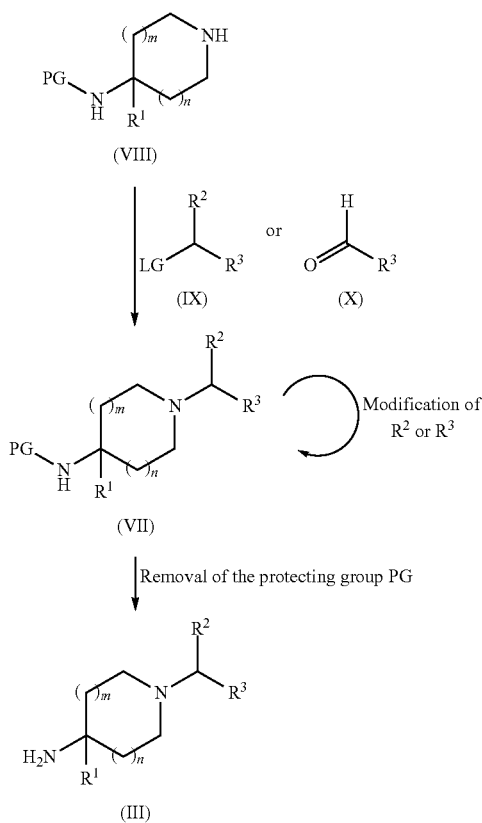

7. EXAMPLES

Where no salt forms of compounds are specified, the compound may exist as a free base or a salt, depending on the synthesis conditions and the processes of workup and purification applied. The skilled person will appreciate that the compound is not limited to the free base or a certain salt form. Where salt forms of compounds are specified, the stoichiometry of the counterion is usually omitted. The skilled person will appreciate that the compound is not limited to the mono salt form and that it may exist as a disalt, trisalt or other compound:counterion stoichiometries. Furthermore, the skilled person will appreciate that such compound may unexpectedly exist as a free base or as a salt with a different counterion, depending on the synthesis conditions and the processes of workup and purification applied. Solely for the purpose of yield determination, an estimate of the nature of the counterion and of compound:counterion stoichieometry is made (as indicated by the formula given).

7.1 SYNTHESIS OF INTERMEDIATES

Intermediate A 3,5-diamino-6-chloropyrazine-2-carboxylic acid

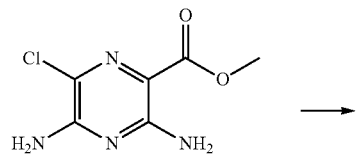

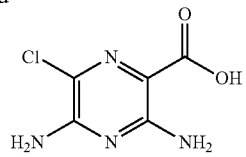

A

A mixture of methyl 3,5-diamino-6-chloropyrazine-2-carboxylate (100 g; 494 mmol), methanol (1 l) and NaOH (6 mol/l in water; 240 mL; 1.44 mol) is refluxed for 3 h. The mixture is allowed to cool to r.t. and then neutralized by addition of hydrochloric acid (6 mol/l in water; approx. 240 mL). Water (200 mL) is added. The precipitate formed is filtered off with suction, washed with water and dried at 60° C.

Yield: 99.6 g (107% of theory)

$C_5H_5ClN_4O_2$

ESI Mass spectrum: m/z=189 [M+H]+; m/z=187 [M−H]−

Intermediate B 1-(tert-butylcarbamoyl)prop-1-en-2-yl 3,5-diamino-6-chloropyrazine-2-carboxylate

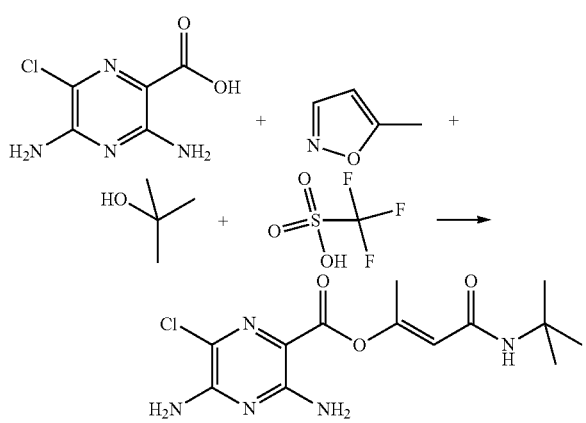

B

Stage 1:

A mixture of tert-butanol (21.0 mL; 226 mmol) and 5-methylisoxazole (18.0 mL; 221 mmol) is cooled with an ice-bath. Trifluoromethanesulphonic acid (20.0 mL; 221 mmol) is added dropwise with continued cooling. The resulting mixture is stirred for 1 h without further cooling.

Stage 2:

To a solution or suspension of 3,5-diamino-6-chloropyrazine-2-carboxylic acid (Intermediate A; 14.0 g; 74.2 mmol) and triethylamine (31.0 mL; 222 mmol) in DMF (100 mL) is added the mixture prepared in stage 1. The resulting mixture is stirred for 4 h at r.t. Ice-water is added with stirring. The precipitate formed is filtered off with suction, washed with water and dried at 65° C. to yield the title compound.

Yield: 18.2 g (75% of theory)

$C_{13}H_{18}ClN_5O_3$

TLC (Silica; DCM/MeOH 9:1): $R_f$=0.4

ESI Mass spectrum: m/z=328 [M+H]+; m/z=326 [M−H]−

Intermediate C

3,5-diamino-6-chloro-N-[(methylsulfanyl)methanimidoyl]pyrazine-2-carboxamide

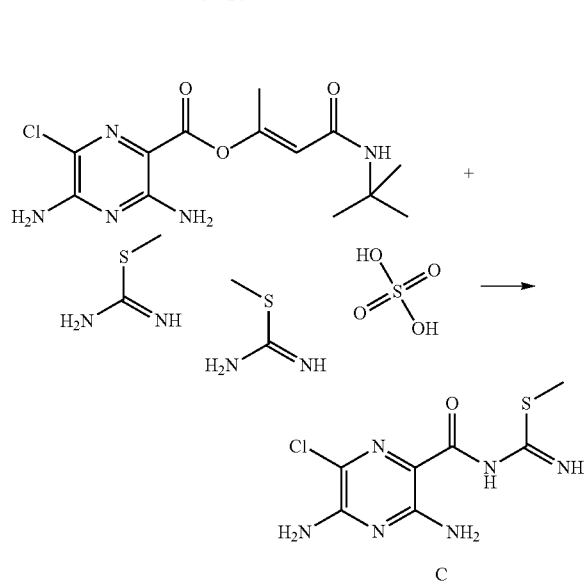

To NaOH (1 mol/l in water; 9.2 mL; 9.2 mmol) is added S-methylisothiourea sulphate (1.78 g; 6.1 mmol. The mixture is stirred until complete solution is achieved. TBME/THF (1:1; 30 mL) and then 1-(tert-butylcarbamoyl)prop-1-en-2-yl 3,5-diamino-6-chloropyrazine-2-carboxylate (Intermediate B; 2.00 g; 6.10 mmol) are added and the mixture is stirred at r.t. over night, then water (6 mL) is added. The precipitate formed is filtered off with suction, washed successively with water, methanol and then with diethyl ether and then dried at 50° C. to yield the title compound.

Yield: 1.33 g (84% of theory)
$C_7H_9ClN_6OS$
ESI Mass spectrum: m/z=261 [M+H]+; m/z=259 [M−H]−

Intermediate I.1

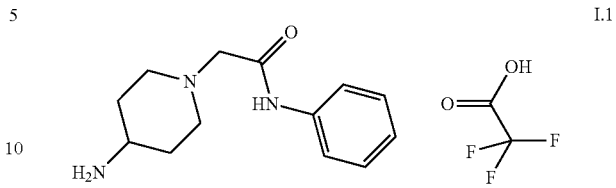

Stage 1:

A mixture of (4-tert-butoxycarbonylaminopiperidin-1-yl) acetic acid (0.50 g; 1.94 mmol), phenylamine (0.18 mL; 1.94 mmol), the coupling reagent TBTU (0.62 g; 1.94 mmol) and DIPEA (0.35 mL; 2.0 mmol) in DMF (5 mL) is stirred at r.t. over night. The solvent is evaporated and the residue is purified by silica gel column chromatography (DCM:MeOH=40:1) to give tert-butyl N-[1-(2-anilino-2-oxo-ethyl)-4-piperidyl]carbamate.

Yield: 0.28 g (43% of theory)
$C_{18}H_{27}N_3O_3$ ESI Mass spectrum: m/z=334 [M+H]+

Stage 2:

The product of stage 1 (0.28 g; 0.84 mmol) is stirred over night at r.t. with 10 mL 10% TFA in DCM. The solvent is removed to give 2-(4-amino-1-piperidyl)-N-phenyl-acetamide as a TFA salt (I.1).

Yield: 0.29 g (99% of theory)
$C_{13}H_{19}N_3O \times C_2HF_3O_2$ ESI Mass spectrum: m/z=234 [M+H]+

The following compounds of general formula I.A are prepared accordingly from starting materials as indicated. Due to conditions applied, the syntheses may yield a free base, a hydrochloride or dihydrochloride salt, a zwitterion or other salt forms which can be applied equally to the syntheses of example compounds described below.

TABLE 1

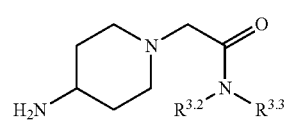

I.A

| Intermediate | $R^{3.2}$ | $R^{3.3}$ | starting material | Synthesis comment |
|---|---|---|---|---|
| I.2 | H | ![structure] | 4-amino-N-methyl-N-(1-methyl-4-piperidyl)benzamide | stage 1 with HATU as coupling reagent |
| I.3 | H | ![structure] | 2-[N-(4.aminophenyl)methanesulfonamido]-N-methylacetamide | stage 1 with HATU as coupling reagent |

TABLE 1-continued

I.A

[Structure: piperidine with 4-amino group and N-CH2-C(=O)-N(R3.2)(R3.3)]

| Intermediate | R3.2 | R3.3 | starting material | Synthesis comment |
|---|---|---|---|---|
| I.4 | H | 4-substituted phenyl-N(CH3)-C(=O)-CH2-N(CH3)2 | N-(4-aminophenyl)-2-dimethylamino-N-methyl-acetamide | stage 1 with HATU as coupling reagent |
| I.5 | H | 4-(piperidin-1-ylmethyl)phenyl | 4-piperidin-1-ylmethyl-phenylamine | stage 1 with HATU as coupling reagent |
| I.6 | H | 3-(morpholin-4-ylmethyl)phenyl | 4-morpholin-4-ylmethyl-phenylamine | stage 1 with HATU as coupling reagent |
| I.7 | H | 4-substituted phenyl-N(C(=O)CH3)-CH2CH2CH2-N(CH3)2 | N-(4-aminophenyl)-N-(3-dimethylamino-propyl)-acetamide | stage 1 with HATU as coupling reagent |
| I.8 | H | 4-substituted phenyl-SO2-N(CH3)-CH2CH2-N(CH3)2 | 4-[N-methyl-N-(2-diemthylamino-ethyl)-aminosulfonyl]aniline | stage 1 with HATU as coupling reagent |
| I.9 | H | 4-substituted phenyl-O-CH2CH2-N(CH2CH3)2 | 4-[2-diethylamino)-ethoxy]aniline | stage 1 with HATU as coupling reagent |
| I.10 | H | 4-substituted phenyl-SO3H | 4-amino-benzenesulfonic acid | stage 1 with HATU as coupling reagent |
| I.11 | H | 4-substituted phenyl-N(SO2CH3)-CH2CH2-N(CH3)2 | N-(4-aminophenyl)-N-(2-dimethylaminoethyl)-methanesufonamide | stage 1 with HATU as coupling reagent |
| I.12 | H | 3-substituted phenyl-SO3H | 3-aminobenzenesulfonic acid | stage 1 with HATU as coupling reagent |

TABLE 1-continued

I.A

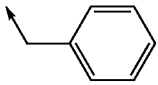

| Intermediate | R<sup>3.2</sup> | R<sup>3.3</sup> | starting material | Synthesis comment |
|---|---|---|---|---|
| I.13 | H | 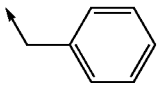 | benzyl-methyl-amine | stage 1 with CDI as coupling reagent |
| I.14 | H | 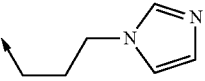 | benzylamine | stage 1 with CDI as coupling reagent |
| I.15 | H | 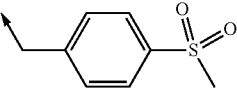 | N-(3-aminopropyl)imidazole | |
| I.16 | H | 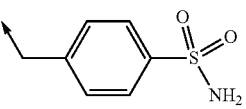 | 4-methylsulfonyl-benzylamine | |
| I.17 | H | 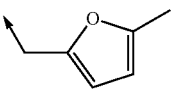 | 4-aminomethyl-benzenesulfonamide | |
| I.18 | H | 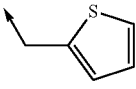 | 5-methyl-2-furanmethanamine | |
| I.19 | H | 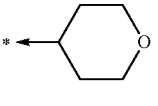 | thiophenemethylamine | |
| I.20 | H |  | 4-aminotetrahydropyran | stage 1 solvent is THF |
| I.21 | H | 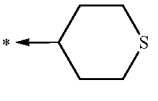 | 2-(ethylthio)ethylamine | |
| I.22 | H | 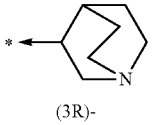 | tetrahydrothiopyran-4-ylamine | stage 1 solvent is THF |
| I.23 | H | <br>(3R)-configuration | (R)-(+)-3-aminoquinuclidine * HCl | |

TABLE 1-continued

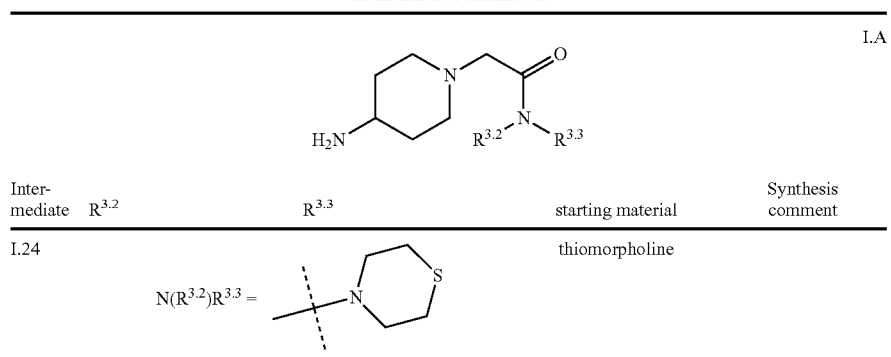

| Intermediate | $R^{3.2}$ | $R^{3.3}$ | starting material | Synthesis comment |
|---|---|---|---|---|
| I.24 | $N(R^{3.2})R^{3.3} =$ 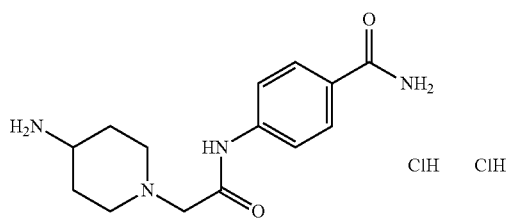 | | thiomorpholine | |

Intermediate II.1

II.1

Stage 1:

A mixture of 4-(2-chloroacetamido)benzamide (0.57 g; 2.68 mmol), tert-butyl piperidin-4-ylcarbamate (0.55 g; 2.68 mmol) and DBU (0.40 mL; 2.68 mmol) in ACN (30 mL) is stirred at r.t. over night. Then the solvent is evaporated and the residue is dissolved in DCM. The solution is washed once with water, then with brine. The organic layer is dried and the solvent is evaporated. The residue is suspended in ether, filtered off with suction and dried to yield tert-butyl 1-(2-(4-carbamoylphenylamino)-2-oxoethyl)piperidin-4-ylcarbamate.

Yield: 0.54 g (54% of theory)
$C_{19}H_{28}N_4O_4$ ESI Mass spectrum: m/z=377 [M+H]+
HPLC analytics: RT=0.80 min (HPLC method 1)

Stage 2:

The intermediate of stage 1 (0.54 g; 1.43 mmol) is stirred for 1 h at r.t. with 20 mL of TFA/DCM 1:4. The solvent is removed and to the residue is added methanolic HCl. Volatiles are evaporated, the residue is suspended in ether, filtered off with suction and dried to give 4-(2-(4-aminopiperidin-1-yl)acetamido)benzamide as a HCl salt (II.1).

Yield: 0.50 g (99.8% of theory)
$C_{14}H_{20}N_4O_2 \times 2HCl$ ESI Mass spectrum: m/z=277 [M+H]+

The following compounds are prepared accordingly from starting materials as indicated. Unless stated otherwise, the amine component applied is tert-butyl N-(piperidin-4-yl)carbamate. Due to conditions applied, the syntheses may yield a free base, a hydrochloride or dihydrochloride salt, a zwitterion or other salt forms which can be applied equally to the syntheses of example compounds as described above.

TABLE 2

| Intermediate | Structure | starting material | Synthesis comment |
|---|---|---|---|
| II.2 | 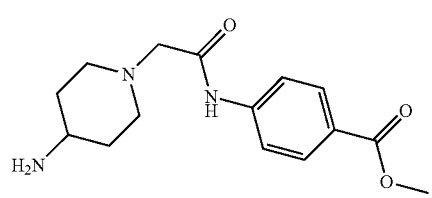 [SMILES: COC(=O)c1ccc(NC(=O)CN2CCC(N)CC2)cc1] | chloro-N-(4-methoxycarbonyl-phenyl)acetamide | |
| II.3 | 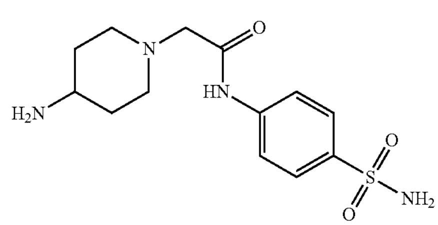 [SMILES: NC1CCN(CC(=O)Nc2ccc(S(N)(=O)=O)cc2)CC1] | 2-chloro-N-(4-sulfamoyl-phenyl)-acetamide | stage 1 with 2 eq DBU |

TABLE 2-continued

| Intermediate | Structure | starting material | Synthesis comment |
|---|---|---|---|
| II.4 | 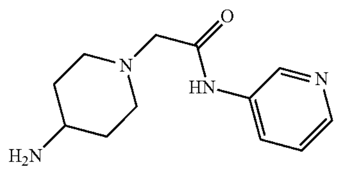 [SMILES: NC1CCN(CC(=O)Nc2cccnc2)CC1] | 2-chloro-N-pyridin-3-yl-acetamide | stage 1 with 2.4 eq $K_2CO_3$ instead of DBU |
| II.5 | 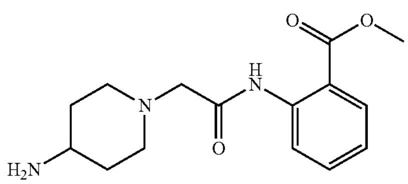 [SMILES: COC(=O)c1ccccc1NC(=O)CN1CCC(N)CC1] | 2-(2-chloro-acetylamino)-benzoic acid methyl ester | |
| II.6 | 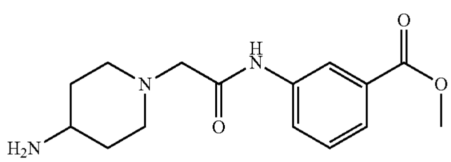 [SMILES: COC(=O)c1cccc(NC(=O)CN2CCC(N)CC2)c1] | 3-(2-chloro-acetylamino)-benzoic acid methyl ester | |
| II.7 | 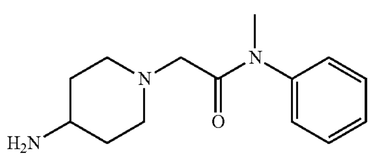 [SMILES: CN(C(=O)CN1CCC(N)CC1)c1ccccc1] | 2-chloro-N-methyl-N-phenyl-acetamide | stage 1 with 1.1 eq DIPEA instead of DBU |
| II.8 | 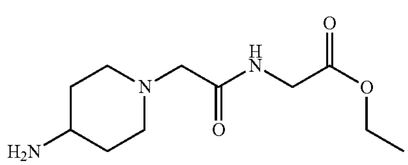 [SMILES: CCOC(=O)CNC(=O)CN1CCC(N)CC1] | N-(chloroacetyl)glycine ethyl ester | stage 1 with 1.2 eq $K_2CO_3$ instead of DBU |
| II.9 | 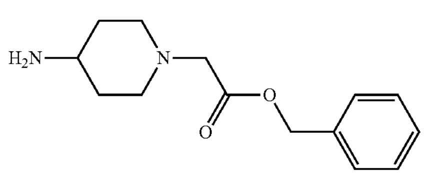 [SMILES: NC1CCN(CC(=O)OCc2ccccc2)CC1] | benzyl bromoacetate | stage 1 with 1.0 eq $K_2CO_3$ instead of DBU |
| II.10 | 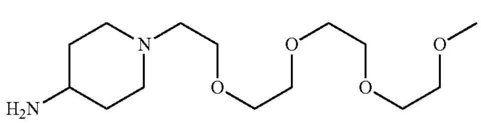 [SMILES: COCCOCCOCCOCCN1CCC(N)CC1] | 2-{2-[2-(2-methoxy-ethoxy)ethoxy]ethoxy}ethylbromide | stage 1 with 2.0 eq $K_2CO_3$ instead of DBU |
| II.11 | 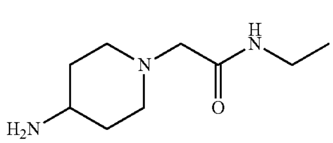 | 2-chloro-N-ethyl acetamide | stage 1 with 1.2 eq $K_2CO_3$ instead of DBU |

Intermediate III.1

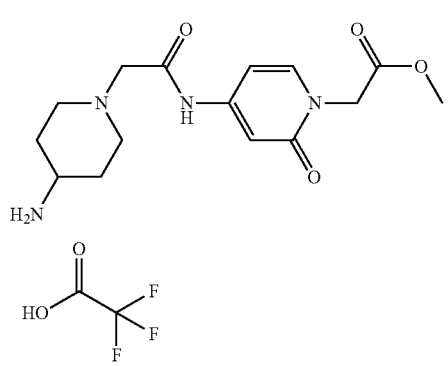

Stage 1:

Tert-butyl N[1-(carbamoylmethyl)piperidin-4-yl]carbamate (0.12 g; 0.47 mmol), (4-iodo-2-oxo-2H-pyridin-1-yl)-acetonitrile (0.13 g; 0.50 mmol), cesium carbonate (0.45 g; 1.38 mmol) and dioxane (10 mL) are mixed and degassed. Tris(dibenzylideneacetone)dipalladium(O) (0.07 g; 0.08 mmol) and Xantphos (0.05 g; 0.09 mmol) are added and degassed again. The reaction mixture is stirred at 90° C. over night. Insoluble material is filtered off with suction and the filtrate is evaporated to dryness. The product is purified via RP HPLC (modifier: $NH_3$).

Stage 2:

The intermediate of stage 1 is dissolved in DCM/TFA and stirred over night. The solvent is removed to yield {4-[2-(4-amino-piperidin-1-yl)acetylamino]-2-oxo-2H-pyridin-1-yl}-acetic acid methyl ester as a TFA salt.

Yield: 0.12 g (83% of theory)

$C_{15}H_{22}N_4O_4 \times C_2HF_3O_2$ ESI Mass spectrum: m/z=323 [M+H]+

The following compound is prepared accordingly from starting materials as indicated. Due to conditions applied, the synthesis may yield a free base, a hydrochloride or dihydrochloride salt, a zwitterion or other salt forms which can be applied equally to the syntheses of example compounds as described above.

TABLE 3

| Intermediate | Structure | Synthesis starting material | comment |
|---|---|---|---|
| III.2 | ![structure] | 4-iodo-1-methyl-1H-pyridin-2-one | |

Intermediate IV.1

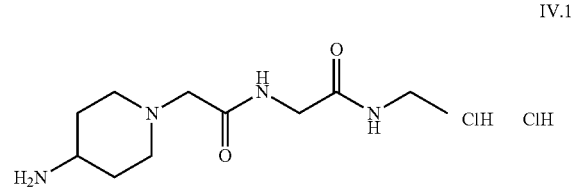 [SMILES: CCNC(=O)CNC(=O)CN1CCC(N)CC1 ; Cl ; Cl]

Stage 1:

A mixture of benzyl bromoacetate (13.73 g; 59.92 mmol), tert-butyl piperidin-4-ylcarbamate (10.00 g; 49.93 mmol) and potassium carbonate (6.89 g; 49.93 mmol) in ACN (300 mL) is stirred at r.t. overnight. The insoluble material is filtered off and the filtrate is evaporated. The residue is solved with DCM. The solution is washed once with brine. The organic layer is dried and the solvent is removed.

Yield: 14.00 g (81% of theory)

$C_{13}H_{28}N_2O_4$ ESI Mass spectrum: m/z=349 [M+H]+

Stage 2:

The intermediate of stage 1 (14.00 g; 40.18 mmol) is hydrogenated in ethanol (250 mL) with Pd—C (10%; 0.34 g; 3.17 mmol) under 3 atm hydrogen pressure in a Parr apparatus over night at r.t.

Catalyst is removed by filtration, extracted with ethanol and the filtrate is evaporated. The residue is suspended in diethyl ether, filtered off with suction and dried. Yield: 10.00 g (92% of theory)

$C_{12}H_{22}N_2O_4$

Stage 3:

A mixture of the intermediate from stage 2 (0.50 g; 1.84 mmol), 2-amino-N-ethylacetamide (0.19 g; 1.84 mmol), TBTU (0.68 g; 2.11 mmol) and triethylamine (0.77 mL; 5.52 mmol) in DMF is stirred at r.t. over night. The solvent is evaporated and the residue is dissolved in DCM. The solution is washed with water and aq. $NaHCO_3$. The organic phase is dried and the solvent is removed.

The residue is dissolved in dioxane (5 mL) and diethyl ether (10 mL) and hydrochloric acid (4M in dioxane; 7.00 mL; 28.00 mmol) is added. The mixture is stirred at r.t. over night. The solvent is removed and the crude product is suspended in ethyl acetate and filtered off.

Yield: 0.19 g (14% of theory)

$C_{11}H_{22}N_4O_2 \times 2$ HCl ESI Mass spectrum: m/z=243 [M+H]+

The following compound is prepared accordingly from starting materials as indicated. Due to conditions applied, the synthesis may yield a free base, a hydrochloride or dihydrochloride salt, a zwitterion or other salt forms which can be applied equally to the syntheses of example compounds as described above.

TABLE 4

| Intermediate | Structure | starting material | Synthesis comment |
|---|---|---|---|
| IV.2 | 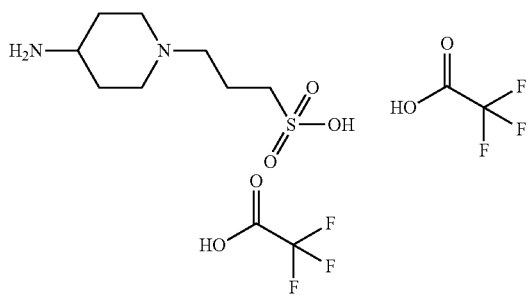 | tert-butyl amine | stage 3: only dioxane used as solvent |

Intermediate V.1

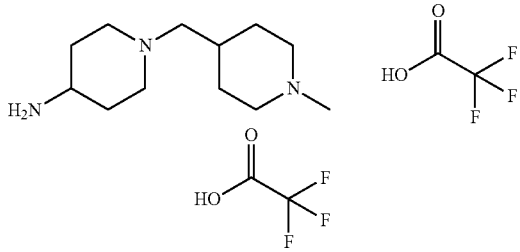

V.1

Stage 1:

A mixture of tert-butyl piperidin-4-ylcarbamate (1.50 g; 7.49 mmol) and 1,3-propanesultone (1.83 g; 14.98 mmol) in ACN (25 mL) is refluxed for 48 h. The solvent is evaporated and the residue is dissolved in water (10 mL). $K_2CO_3$ (approx. 1 g) is added in portions until gas evolution has ceased. The mixture is heated to 60° C. for 15 minutes and then allowed to cool to r. t., diluted with ACN (15 mL) and finally kept at 4° C. for 48 h. The precipitate is filtered off, washed with diethyl ether and dried Yield: 0.95 g (75% of theory)

$C_{13}H_{26}N_2O_5S$ ESI Mass spectrum: m/z=322 [M+H]+

Stage 2:

The intermediate from stage 1 is dissolved in DCM (25 mL) and TFA (2.5 mL) is added. The resulting solution is stirred at r.t. for several hours, then diethyl ether (30 mL) is added. The precipitate formed is collected by filtration and dried. The title compound is yielded as a TFA salt.

Yield: 1.10 g (78% of theory)

$C_8H_{18}N_2O_5S \times 2C_2HF_3O_2$ ESI Mass spectrum: m/z=223 [M+H]+

Intermediate VI.1

VI.1

Stage 1:

A mixture of tert-butyl piperidin-4-ylcarbamate (0.25 g; 1.25 mmol) and 1-methylpiperidine-4-carbaldehyde*HCl (0.20 g; 1.25 mmol) in DCM (20 mL) is stirred for 1.5 h at r.t. Sodium triacetoxyborohydride (0.36 g; 1.62 mmol) is added. After stirring over night at r.t. the mixture is diluted with further DCM (20 mL) and washed twice with hydrochloric acid (1M). The organic layer is separated, dried and evaporated to dryness.

Yield: 200 mg (51% of theory)

$C_{17}H_{33}N_3O_2$

Stage 2:

The product from stage 1 is dissolved in DCM and TFA is added. The resulting solution is stirred at r.t. for 2 h. The solvent is removed to yield the title compound as a TFA salt.

Yield: 300 mg (55% of theory)

$C_{12}H_{25}N_3 * 2C_2HF_3O_2$

Intermediate VII.1

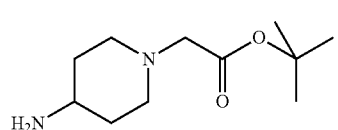

VII.1

Stage 1:

A mixture of piperidin-4-ylcarbamic acid benzyl ester*HCl (5.00 g; 18.47 mmol), tert-butyl bromoacetate (4.14 g; 21.24 mmol) and potassium carbonate (6.37 g; 46.17 mmol) in ACN (100 mL) is stirred for 1 day at r.t. Insoluble material is filtered off and the filtrate is evaporated.

Yield: 6.50 g (96% of theory)

$C_{19}H_{28}N_2O_4$ ESI Mass spectrum: m/z=349 [M+H]+

Stage 2:

The intermediate from stage 1 (6.50 g; 17.72 mmol) is hydrogenated with Pd—C (10%; 0.60 g) in ethanol (100 mL) under 2 atm hydrogen pressure in a Parr apparatus for 5 h at r.t. The catalyst is removed by filtration and the filtrate is evaporated to dryness.

Yield: 4.2 g (83% of theory)

$C_{11}H_{22}N_2O_2$ ESI Mass spectrum: m/z=215 [M+H]+

Intermediate VIII.1

VIII.1

Stage 1:
A mixture of tert-butyl piperidin-4-ylcarbamate (5.00 g; 20.91 mmol), diethyl bromomalonate (4.19 g; 20.91 mmol) and potassium carbonate (4.34 g; 31.37 mmol) in ACN (150 mL) is stirred for 1 day at r.t. Insoluble material is filtered off and the filtrate is evaporated. The residue is dissolved in DCM and washed with water and brine. The organic layer is separated, dried and the solvent is evaporated.
Yield: 7.10 g (78% of theory)
$C_{17}H_{30}N_2O_6$

Stage 2:
The intermediate from stage 1 (0.50 g; 1.39 mmol) is dissolved in diethyl ether (15 mL) and hydrogen chloride (4M; in dioxane; 3.49 mL; 13.95 mmol). After stirring over night at r.t. the formed precipitate is filtered off, washed with a small amount of diethyl ether and dried.
Yield: 320 mg (65% of theory)
$C_{12}H_{22}N_2O_4 \times HCl$ ESI Mass spectrum: m/z=259 [M+H]+

Intermediate IX.1

IX.1

Stage 1:
Stage 1 is performed as described for intermediate VIII.1

Stage 2:
The product of stage 1 (0.50 g; 1.39 mmol) and benzylamine (0.76 mL; 6.97 mmol) are stirred in a microwave for 1 h at 140° C. The mixture is diluted with diethyl ether and washed with water. The organic layer is separated, dried and the solvent is removed.
Yield: 0.39 g (50% of theory)
$C_{27}H_{36}N_4O_4$ ESI Mass spectrum: m/z=481 [M+H]+

Stage 3:
The intermediate of stage 2 (0.39 g; 0.70 mmol) is dissolved in methanol (4 mL) and hydrochloric acid (2M; 6.98 mL; 13.96 mmol). After stirring over night at r.t. the precipitate formed is filtered off, washed with a small amount of diethyl ether and dried.
Yield: 350 mg (94% of theory)
$C_{22}H_{28}N_2O_4 \times 2$ HCl ESI Mass spectrum: m/z=381 [M+H]+

Intermediate X.1

X.1

Stage 1:
A mixture of 3-(2-amino-ethyl)benzoic acid ethyl ester hydrochloride (3.00 g; 13.06 mmol), chloroacetylchloride (1.09 mL; 13.71 mmol) and TEA (3.72 mL; 26.77 mmol) in DCM (30 mL) is stirred for 4 h at r.t. The organic layer is extracted with water and saturated aqueous $NaHCO_3$ solution. The organic layer is separated, dried and evaporated to dryness.
Yield: 1.20 g (29% of theory)
$C_{13}H_{16}ClNO_3$ ESI Mass spectrum: m/z=270 [M+H]+

Stage 2:
The intermediate of stage 1 (0.80 g; 2.52 mmol), tert-butyl N-(piperidin-4-yl)carbamate (0.50 g; 2.52 mmol) and potassium carbonate (0.35 g; 2.52 mmol) in ACN (20 mL) are stirred for 2 days at r.t. Insoluble material is filtered off and washed with ethylacetate/hexane (v/v=1:1). The filtrate is evaporated.
Yield: 1.15 g (63% of theory)
$C_{23}H_{35}N_3O_5$ ESI Mass spectrum: m/z=434 [M+H]+

Stage 3:
The intermediate of stage 2 (1.15 g; 1.59 mmol) and HCl (2M in diethylether; 15.92 mL; 31.83 mmol) are stirred overnight. The precipitate formed is filtered off with suction and washed with diethyl ether to yield the title compound as a HCl salt.
Yield: 0.63 g (93% of theory)
$C_{18}H_{27}N_3O_3 \times 2HCl$ ESI Mass spectrum: m/z=334 [M+H]+

Intermediate XI.1

XI.1

Stage 1:
A mixture of tert-butyl N-(piperidin-4-yl)carbamate hydrochloride (2.50 g; 11.28 mmol), chloroacetylchloride (0.99 mL; 12.40 mmol) and TEA (3.29 mL; 23.68 mmol) in DCM (50 mL) is stirred for 5 h at r.t. The organic layer is extracted with water and hydrochloric acid (0.1 M). The organic layer is separated, dried and evaporated to dryness.
Yield: 2.70 g (82% of theory)
$C_{12}H_{20}ClNO_3$ ESI Mass spectrum: m/z=262 [M+H]+

Stage 2:
The intermediate of stage 1 (1.60 g; 6.83 mmol), 4-benzyloxycarbonylamino-piperidine (2.18 g; 7.51 mmol) and potassium carbonate (1.42 g; 10.24 mmol) in ACN (40 mL) are stirred at r.t. After stirring over night the insoluble material is filtered off and the filtrate is evaporated to dryness.
Yield: 3.10 g (84% of theory)
$C_{25}H_{37}N_3O_5$ ESI Mass spectrum: m/z=460 [M+H]+

Stage 3:

The intermediate of stage 2 (3.00 g; 5.55 mmol) in ethanol (50 mL) and hydrochloric acid (37%; 1 mL) is hydrogenated with Pd—C (10%; 0.59 g; 0.55 mmol) under 3 atm hydrogen pressure in a Parr apparatus for 3 days at r.t. The catalyst is removed by filtration through celite and volatiles are removed under reduced pressure to yield the title compound as a HCl salt.

Yield: 1.90 g (82% of theory)

$C_{17}H_{31}N_3O_3 \times 2HCl$ ESI Mass spectrum: m/z=326 [M+H]+

7.2 SYNTHESIS OF EXAMPLES

Example 1.1

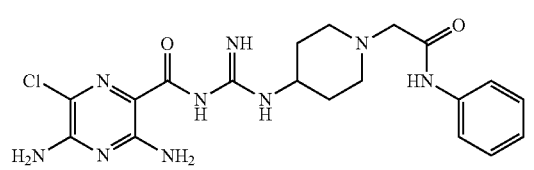

1.1

A mixture of 3,5-diamino-6-chloro-N-[(methylsulfanyl)methanimidoyl]pyrazine-2-carboxamide (Intermediate C; 0.08 g; 0.31 mmol), the primary amine 2-(4-aminopiperidin-1-yl)-N-phenylacetamide as a TFA salt (Intermediate 1.1; 0.11 g; 0.31 mmol) and TEA (0.17 mL; 1.23 mmol) in THF (2 mL) is stirred for 3 h at 70° C. After one night stirring at r.t. volatiles are evaporated and the residue is purified by silica gel column chromatography (DCM/Methanol 6:1). The product is treated with methanolic HCl, evaporated to dryness, suspended in ether, filtered off with suction and dried to yield the title compound as a HCl salt.

Yield: 83 mg (56% of theory)

$C_{19}H_{24}ClN_9O_2 \times HCl$ ESI Mass spectrum: m/z=446 [M+H]+

HPLC analytics: RT=0.81 min (HPLC method 2)

The following compounds of general formula 1.A are prepared accordingly using the respective primary amine as indicated. Due to conditions applied, the syntheses may yield a free base, a hydrochloride or dihydrochloride salt, a zwitterion or other salt forms which can be applied equally to the syntheses of example compounds as described above.

TABLE 5

1.A

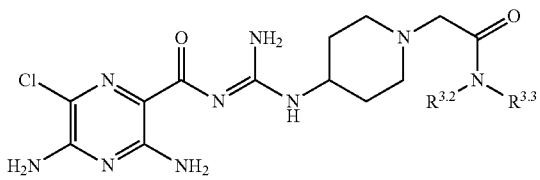

| Example | $R^{3.2}$ | $R^{3.3}$ | Primary amine applied: | Synthesis comment | ESI mass spectrum | HPLC Retention time (min) | HPLC method |
|---|---|---|---|---|---|---|---|
| 1.2 | H | NH2) | II.1 | see footnote a | 489 (M + H)+ | 0.72 | 3 |
| 1.3 | H | O-) | II.2 | | 405 (M + H)+ | 0.89 | 3 |
| 1.4 | H | 2NH2) | II.3 | | 525 (M + H)+ | 0.63 | 2 |
| 1.5 | H | ![methylpiperidinyl benzamide] | I.2 | solvent is DMF | 600 (M + H)+ | 0.48 | 4 |

TABLE 5-continued
1.A
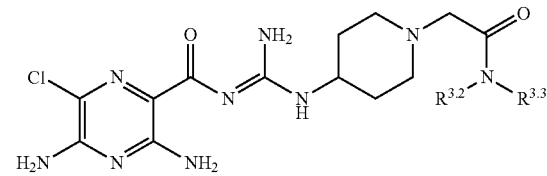
| Example | R[3.2] | R[3.3] | Primary amine applied: | Synthesis comment | ESI mass spectrum | HPLC Retention time (min) | HPLC method |
|---|---|---|---|---|---|---|---|
| 1.6 | H | 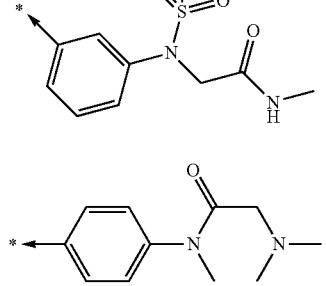 | I.3 | see footnote b | 608 (M + H)+ | 0.52 | 4 |
| 1.7 | H | 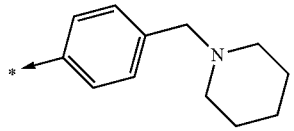 | I.4 | see footnote b | 560 (M + H)+ | 0.49 | 4 |
| 1.8 | H | 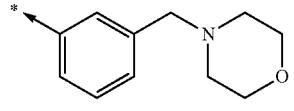 | I.5 | see footnote b | 543 (M + H)+ | 0.50 | 4 |
| 1.9 | H | 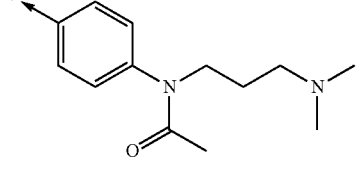 | I.6 | see footnote b | 545 (M + H)+ | 0.49 | 4 |
| 1.10 | H | 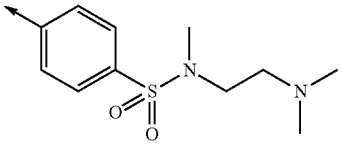 | I.7 | see footnote c | 588 (M + H)+ | 0.49 | 4 |
| 1.11 | H | 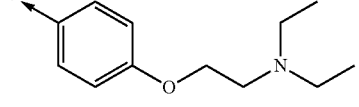 | I.8 | see footnote c | 610 (M + H)+ | 0.47 | 4 |
| 1.12 | H | 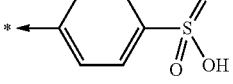 | I.9 | see footnote c | 561 (M + H)+ | 1.01 | 5 |
| 1.13 | H |  | I.10 | see footnote b | 526 (M + H)+ | 0.44 | 6 |

TABLE 5-continued

1.A

| Example | $R^{3.2}$ | $R^{3.3}$ | Primary amine applied: | Synthesis comment | ESI mass spectrum | HPLC Retention time (min) | HPLC method |
|---|---|---|---|---|---|---|---|
| 1.14 | H | 4-[N-(2-dimethylaminoethyl)-N-methylsulfonyl]phenyl | I.11 | see footnote c | 610 (M + H)+ | 0.66 | 6 |
| 1.15 | H | 1-methyl-2-oxo-pyridin-4-yl | III.2 | see footnote d | 477 (M + H)+ | 0.67 | 3 |
| 1.16 | H | 1-(methoxycarbonylmethyl)-2-oxo-pyridin-4-yl | III.1 | see footnote d | 535 (M + H)+ | 1.06 | 5 |
| 1.17 | H | pyridin-3-yl | II.4 | see footnote c | 447 (M + H)+ | 6.27 | 7 |
| 1.18 | H | 2-(methoxycarbonyl)phenyl | II.5 | see footnote b | 504 (M + H)+ | 1.55 | 5 |
| 1.19 | H | 3-(methoxycarbonyl)phenyl | II.6 | see footnote b | 504 (M + H)+ | 0.89 | 3 |
| 1.20 | H | 3-sulfophenyl | I.12 | see footnote b | 526 (M + H)+ | 0.45 | 6 |
| 1.21 | $CH_3$ | benzyl | I.13 | | 474 (M + H)+ | 0.83 | 2 |
| 1.22 | $CH_3$ | phenyl | II.7 | see footnote b | 460 (M + H)+ | 0.77 | 2 |

TABLE 5-continued

1.A

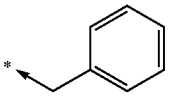

| Example | R³·² | R³·³ | Primary amine applied: | Synthesis comment | ESI mass spectrum | HPLC Retention time (min) | HPLC method |
|---|---|---|---|---|---|---|---|
| 1.23 | H | 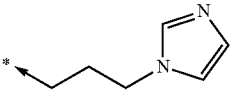 | I.14 | | 460 (M + H)+ | 0.83 | 2 |
| 1.24 | H | 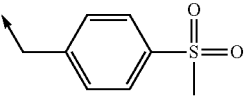 | I.15 | see footnote d | 478 (M + H)+ | 0.76 | 8 |
| 1.25 | H | 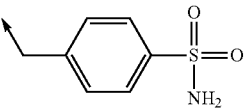 | I.16 | solvent is DMF; see footnote d | 538 (M + H)+ | 1.21 | 9 |
| 1.26 | H | 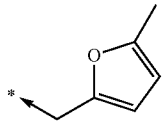 | I.17 | solvent is DMF, see footnote d | 539 (M + H)+ | 4.50 | 10 |
| 1.27 | H | 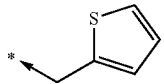 | I.18 | solvents are DMF, 2-propanol, water, see footnote d | 464 (M + H)+ | 1.48 | 9 |
| 1.28 | H | 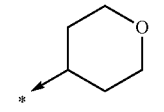 | I.19 | solvent is DMF, see footnote d | 466 (M + H)+ | 1.36 | 9 |
| 1.29 | H | 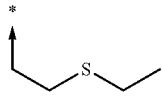 | I.20 | solvent is DMF, see footnote f | 454 (M + H)+ | 1.03 | 9 |
| 1.30 | H | 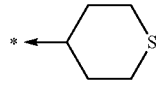 | I.21 | solvent is DMF, see footnote f | 458 (M + H)+ | 1.27 | 9 |
| 1.31 | H | 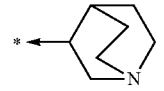 | I.22 | solvent is DMF, see footnote d | 470 (M + H)+ | 1.19 | 9 |
| 1.32 | H |  see footnote e | I.23 | solvent is DMF, see footnote f | 479 (M + H)+ | 0.96 | 9 |
| 1.33 | H |  | II.11 | solvent is DMF, see footnote c | 398 (M + H)+ | 6.10 | 7 |

TABLE 5-continued

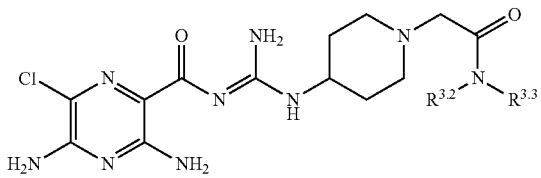

1.A

| Example | R3.2 | R3.3 | Primary amine applied: | Synthesis comment | ESI mass spectrum | HPLC Retention time (min) | HPLC method |
|---|---|---|---|---|---|---|---|
| 1.34 | H | *—CH2CH2-(3-ethoxycarbonylphenyl) | X.1 | solvent is DMF, see footnote f | 546 (M + H)+ | 5.68 | 10 | a: ACN, DIPEA, DMSO, microwave 130° C. 10 min, purification via HPLC, H2O/MeOH, modifier TFA, stationary phase Sunfire C18
b: purification via RP-HPLC (modifier TFA)
c: purification via RP-HPLC (modifier NH3)
d: purification via silica gel column chromatography (DCM/Methanol/NH3)
e: (3R)-configuration
f: purification via RP-HPLC (modifier ammonium formate)

Example 2.1

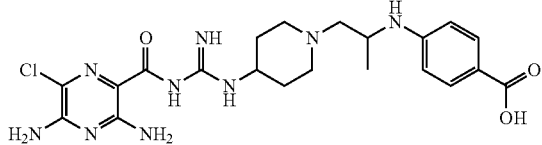

2.1

A mixture of Example 1.3 (0.13 g; 0.24 mmol) and aq. sodium hydroxide (4M; 1.50 mL; 6.00 mmol) in methanol (6 mL) is stirred for 2 h at 80° C.

The mixture is neutralized with an equimolar amount of aq. HCl. The solvent is removed. The residue is suspended in DMF, filtered off and further purified by RP HPLC (modifier: TFA). The product is suspended in ether, filtered off with suction and dried.

Yield: 9 mg (8% of theory)

$C_{20}H_{24}ClN_9O_4$ ESI Mass spectrum: m/z=490 [M+H]+

HPLC analytics: RT=1.1 min (HPLC method 5)

The following compounds of general formula 2.A are prepared accordingly using the respective benzoic acid methyl ester as indicated. Due to conditions applied, the syntheses may yield a free base, a hydrochloride or dihydrochloride salt, a zwitterion or other salt forms which can be applied equally to the syntheses of example compounds as described above.

TABLE 6

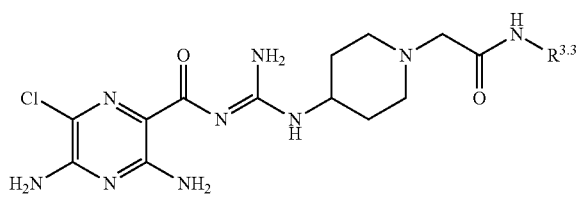

2.A

| Example | R3.3 | ester applied: | Synthesis comment | ESI mass spectrum | HPLC Retention time (min) | HPLC method |
|---|---|---|---|---|---|---|
| 2.2 | 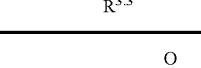 | 1.19 | see footnote a | 490 (M + H)+ | 1.1 | 5 |

TABLE 6-continued

![structure 2.A]

| Example | R[3.3] | ester applied: | Synthesis comment | ESI mass spectrum | HPLC Retention time (min) | HPLC method |
|---|---|---|---|---|---|---|
| 2.3 | *-C6H4-COOH (ortho) | 1.18 | see footnote a, c | 490 (M + H)+ | 1.62 | 5 |
| 2.4 | *-CH2CH2-C6H4-COOH (meta) | 1.34 | see footnote b | 518 (M + H)+ | 2.15 | 9 | a: use of 1M aq. sodium hydroxide; stirred at r.t. for 3 days
b: use of hydrochloric acid (4M); stirred over night at 70° C.; solvent evaporated; residue levigated with ACN; filtered off and dried
c: purification: solvent evaporated; residue levigated with water; filtered off and dried Example 3.1

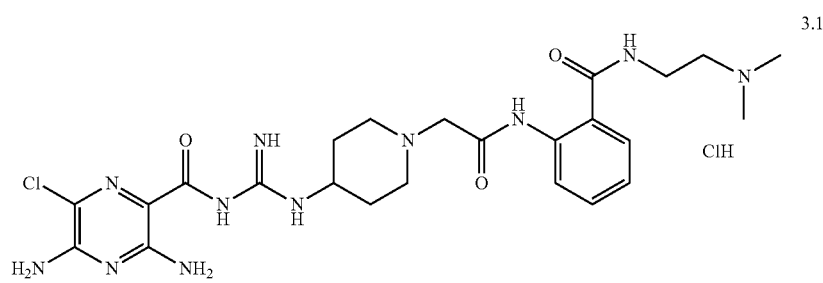 [SMILES: CN(C)CCNC(=O)c1ccccc1NC(=O)CN1CCC(NC(=N)NC(=O)c2nc(Cl)c(N)nc2N)CC1 ; Cl]

A mixture of Example 2.3 (0.13 g; 0.27 mmol), N,N-dimethyl-ethane-1,2-diamine (0.03 mL; 0.27 mmol), DIPEA (0.09 mL; 0.54 mmol) and HATU (0.10 g; 0.27 mmol) in DMF (3 mL) is stirred for 1 week at r.t. The mixture is purified by RP HPLC (modifier: TFA). The product is dissolved in hydrochloric acid (4M; in methanol) and then evaporated to yield the title compound as a HCl salt.

Yield: 50 mg (32% of theory)

$C_{24}H_{34}ClN_{11}O_4 \times HCl$ ESI Mass spectrum: m/z=560 [M+H]+

HPLC analytics: RT=0.73 min (HPLC method 3)

Example 4.1

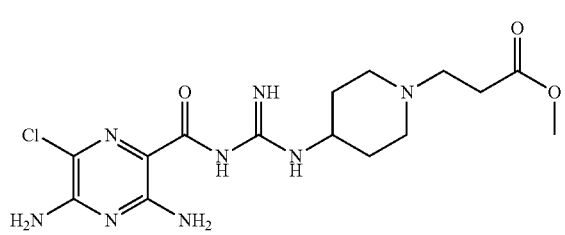

A mixture of 3,5-diamino-6-chloro-N-[(methylsulfanyl)methanimidoyl]pyrazine-2-carboxamide (Intermediate C; 0.20 g; 0.71 mmol), the primary amine 3-(4-amino-piperidin-1-yl)propionic acid methyl ester (0.25 g; 0.87 mmol) and TEA (0.51 mL; 3.64 mmol) in THF (20 mL) is stirred for 1 week at 80° C. The solvent is removed and the residue is taken up in acetonitrile/methanol and filtered. The crude product is purified by RP-HPLC (modifier: NH₄COOH).

Yield: 55 mg (20% of theory)

$C_{15}H_{23}ClN_8O_3$ ESI Mass spectrum: m/z=399 [M+H]+

HPLC analytics: RT=6.77 min (HPLC method 7)

The following compounds of general formula 4.A are prepared accordingly using the respective primary amine as indicated. Due to conditions applied, the syntheses may yield a free base, a hydrochloride or dihydrochloride salt, a zwitterion or other salt forms which can be applied equally to the syntheses of example compounds as described above.

TABLE 7

4.A

| Example | R² / R³ structure | Primary amine applied: | Synthesis comment | ESI mass spectrum | HPLC Retention time (min) | HPLC method |
|---|---|---|---|---|---|---|
| 4.2 | *—CH₂—S—CH₂CH₃ (ethylsulfanyl ethyl) | 1-(2-ethylsulfanyl-ethyl)-piperidin-4-ylamine | use of 4 eq. K₂CO₃ instead of TEA; solvent is DMF | 401 (M + H)+ | 7.96 | 7 |
| 4.3 | *—CH₂—S(O)₂—CH₂CH₃ | 1-(2-ethanesulfonyl-ethyl)-piperidin-4-ylamine | use of 4 eq. K₂CO₃ instead of TEA; solvent is DMF; see footnote a | 433 (M + H)+ | 5.80 | 7 |
| 4.4 | *—CH₂—C(O)—NH—CH₂—C(O)—O—CH₂CH₃ | II.8 | solvent is DMF | 456 (M + H)+ | 6.67 | 7 |
| 4.5 | *—CH₂—C(O)—N(CH₂CH₃)₂ | 2-(4-amino-piperidin-1-yl)-N,N-diethyl-acetamide | additional use of 0.5 eq DMAP, see footnote b | 426 (M + H)+ | 7.33 | 7 |
| 4.6 | *—CH₂—C(O)—O—CH₂CH₃ | (4-amino-piperidin-1-yl)-acetic acid ethyl ester | | 399 (M + H)+ | 6.87 | 7 |
| 4.7 | *—CH₂CH₂—morpholine | 1-(2-morpholin-4-yl-ethyl)-piperidin-4-ylamine | see footnote c | 426 (M + H)+ | 0.97 | 11 |
| 4.8 | *—CH₂CH₂CH₂—C(O)—O—CH₃ | 4-(4-amino-piperidin-1-yl)-butyric acid methyl ester | | 413 (M + H)+ | 7.20 | 7 |

TABLE 7-continued

4.A

| Example | *R²⟵R³ | Primary amine applied: | Synthesis comment | ESI mass spectrum | HPLC Retention time (min) | HPLC method |
|---|---|---|---|---|---|---|
| 4.9 | 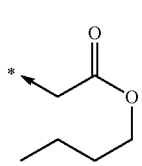 | II.9 | see footnote d | 461 (M + H)+ | 8.38 | 7 |
| 4.10 | 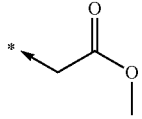 | (4-amino-piperidin-1-yl)acetic acid butyl ester | see footnote d | 427 (M + H)+ | 8.27 | 7 |
| 4.11 | 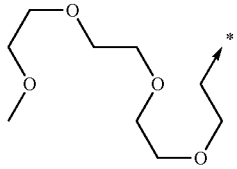 | (4-amino-piperidin-1-yl)acetic acid methyl ester | | 385 (M + H)+ | 6.25 | 11 |
| 4.12 | 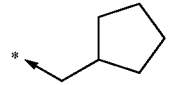 | II.10 | use of 4 eq. K₂CO₃ instead of TEA; solvent is DMF | 503 (M + H)+ | 7.98 | 11 |
| 4.13 |  | 4-amino-1-cyclopenty-methyl-piperidin * 2 HCl | see footnote e | 395 (M + H)+ | 1.05 | 12 |
| 4.14 | *⟵ | 1-ethyl-piperidin-4-ylamine | solvents are THF/ethanol (v/v = 2:1), see footnote d | 341 (M + H)+ | ? | |
| 4.15 | 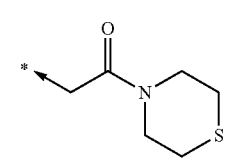 | I.24 | solvent is DMF | 456 (M + H)+ | 1.11 | 9 |
| 4.16 | 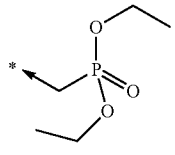 | (4-amino-piperidin-1-ylmethyl)-phosphonic acid diethyl ester | see footnote d | 463 (M + H)+ | 0.80 | 2 |

TABLE 7-continued

4.A

[Structure: chloro-diamino-pyrazine carboxamide with guanidine linked to 4-aminopiperidine bearing N-CH(R²)(R³) substituent]

| Example | *―CH(R²)(R³) | Primary amine applied: | Synthesis comment | ESI mass spectrum | HPLC Retention time (min) | HPLC method |
|---|---|---|---|---|---|---|
| 4.17 | [4-(N-methylpiperidinyl)methyl] | VI.1 | solvents are THF/ethanol (v/v = 2:1), see footnote e | 424 (M + H)+ | 0.82 | 5 |
| 4.18 | [CH₂C(O)O-tBu] | VII.1 | | 427 (M + H)+ | 8.07 | 7 |
| 4.19 | [CH(CO₂Et)₂] | VIII.1 | use of 2.5 eq DIPEA instead of TEA; solvent is DMF | 471 (M + H)+ | 6.71 | 9 |
| 4.20 | [CH(C(O)NHBn)₂] | IX.1 | use of 2.5 eq DIPEA instead of TEA; solvent is DMF | 593 (M + H)+ | 5.84 | 10 |
| 4.21 | [CH₂C(O)NHCH₂C(O)NHEt] | IV.1 | solvent is DMF | 155 (M + H)+ | 1.10 | 9 |
| 4.22 | [CH₂C(O)NH-tBu] | IV.2 | solvent is DMF | 426 (M + H)+ | 1.27 | 9 |
| 4.23 | [(CH₂)₃S(O)₂CH₃] | V.1 | solvent is DMF, use of 4.0 eq K₂CO₃ instead of TEA | 435 (M + H)+ | 1.20 | 11 |

TABLE 7-continued

4.A

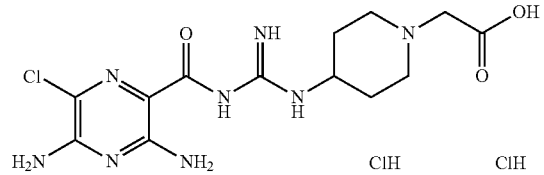

| Example | *—R²/R³ | Primary amine applied: | Synthesis comment | ESI mass spectrum | HPLC Retention time (min) | HPLC method |
|---|---|---|---|---|---|---|
| 4.24 | (piperidine-N-acetyl, 4-tert-butyl ester) | XI.1 | solvent is DMF | 538 (M + H)+ | 5.60 | 10 | a: the primary amine is synthesized by oxidation with MCPBA of the amine used in example 4.2
b: prepared analogously from 2-chloro-N,N-diethylacetamide
c: prepared analogously from N-(2-chloroethyl)morpholine hydrochloride
d: purification via RP-HPLC (modifier TFA)
e: pruification via RP-HPLC (modifier NH₃)

Example 5.1

5.1

A mixture of Example 4.6 (0.40 g; 0.10 mmol) in hydrochloric acid (6 M, 4 mL) is heated at 70° C. for 16 h. After cooling the resulting mixture is freeze-dried. The residue is dissolved in a mixture of ACN/H₂O (1:1 v/v) and filtered through a pad of alumina (Alox B). Volatiles are removed and the residue is suspended in ether, filtered off with suction and dried.

Yield: 23 mg (52% of theory)

$C_{13}H_{19}ClN_8O_3$*×HCl ESI Mass spectrum: m/z=371 [M+H]+

HPLC analytics: RT=2.37 min (HPLC method 7)

The following compounds of general formula 5.A are prepared accordingly using the respective benzoic acid methyl ester as indicated. Due to conditions applied, the syntheses may yield a free base, a hydrochloride or dihydrochloride salt, a zwitterion or other salt forms which can be applied equally to the syntheses of example compounds as described above.

TABLE 8

5.A

| Example | *—R²/R³ | Benzoic acid methyl ester applied: | Synthesis comment | ESI mass spectrum | HPLC Retention time (min) | HPLC method |
|---|---|---|---|---|---|---|
| 5.2 | (acetyl-NH-CH₂-COOH) | 4.4 | | 428 (M + H)+ | 1.05 | 11 |

TABLE 8-continued

5.A

![Structure 5.A]

| Example | *—R² / R³ | Benzoic acid methyl ester applied: | Synthesis comment | ESI mass spectrum | HPLC Retention time (min) | HPLC method |
|---|---|---|---|---|---|---|
| 5.3 | *—CH₂CH₂CH₂C(=O)OH | 4.8 | | 399 (M + H)+ | 2.92 | 7 |
| 5.4 | *—CH₂C(=O)—N(piperidine-4-COOH) | 4.24 | use of HCl (4M in dioxane) and diethyl ether as solvent, see footnote a | 482 (M + H)+ | 0.98 | 10 | a: purification: formed precipitate is filtered off, washed with acetone and dried Example 6.1

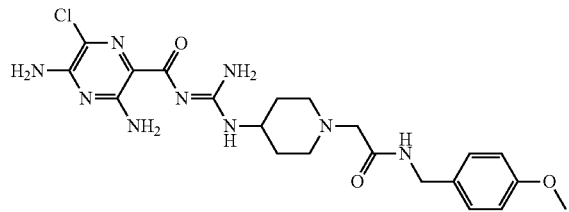

A mixture of Example 5.1 (0.15 g; 0.28 mmol), 4-methoxy-benzylamine (0.04 g; 0.31 mmol), O-(benzotriazol-1-yl)-N,N,N',N'-tetramethyluronium tetrafluoroborate (0.10 g; 0.32 mmol) and DIPEA (0.15 mL; 0.84 mmol) in DMF (2 mL) is stirred over night at r.t. under nitrogen atmosphere. H₂O (1 mL) is added. The reaction mixture is purified via RP HPLC (modifier NH₄COOH).

Yield: 105 mg (76% of theory)
$C_{21}H_{28}ClN_9O_3$ ESI Mass spectrum: m/z=490 [M+H]+
HPLC analytics: RT=7.62 min (HPLC method 7)

The following compounds of general formula 6.A are prepared accordingly using the respective primary amine as indicated. Due to conditions applied, the syntheses may yield a free base, a hydrochloride or dihydrochloride salt, a zwitterion or other salt forms which can be applied equally to the syntheses of example compounds as described above.

TABLE 9

6.A

| Example | R³·² | R³·³ | Primary amine applied: | ESI mass spectrum | HPLC Retention time (min) | HPLC method |
|---|---|---|---|---|---|---|
| 6.2 | * (methyl, with methoxyethyl branch) | *—CH₂CH₂OCH₃ | bis (2-methoxy-ethyl)amine | 486 (M + H)+ | 6.78 | 7 |

TABLE 9-continued

6.A

| Example | R3.2 | R3.3 | Primary amine applied: | ESI mass spectrum | HPLC Retention time (min) | HPLC method |
|---|---|---|---|---|---|---|
| 6.3 | H | 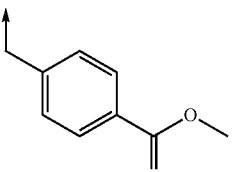 | 2-(trifluoromethylthio)benzylamine | 560 (M + H)+ | 8.62 | 7 |
| 6.4 | H | 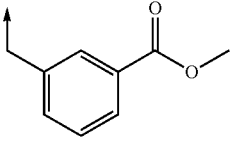 | 4-(aminomethyl)benzoic acid methyl ester * HCl | 518 (M + H)+ | 7.45 | 7 |
| 6.5 | H | 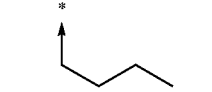 | 3-(aminomethyl)benzoic acid methyl ester * HCl | 518 (M + H)+ | 7.51 | 7 |
| 6.6 | H | 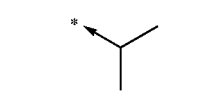 | butylamine | 426 (M + H)+ | 1.24 | 11 |
| 6.7 | H | 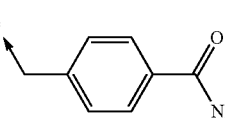 | isopropylamine | 412 (M + H)+ | 1.12 | 11 |
| 6.8 | H | 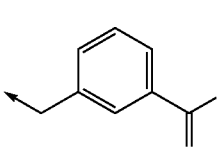 | 4-aminomethyl-benzamide | 503 (M + H)+ | 6.14 | 7 |
| 6.9 | H | 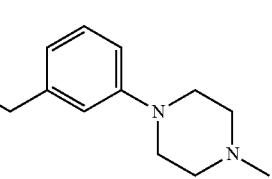 | 3-aminomethyl-benzamide | 503 (M + H)+ | 6.25 | 7 |
| 6.10 | H |  | 1-[3-(4-methyl-piperazin-1-yl)phenyl]methylamine | 558 (M + H)+ | 0.96 | 11 |

TABLE 9-continued

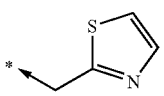

6.A

| Example | $R^{3.2}$ | $R^{3.3}$ | Primary amine applied: | ESI mass spectrum | HPLC Retention time (min) | HPLC method |
|---|---|---|---|---|---|---|
| 6.11 | H |  | 2-aminomethyl-thiazole * HCl | 467 (M + H)+ | 6.51 | 7 |
| 6.12 | H | *＼＼＼＼O＼ | 2-methoxyethyl-amine | 428 (M + H)+ | 1.09 | 11 |
| 6.13 | H | 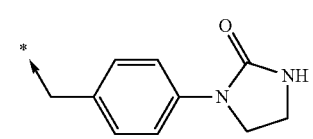 | see footnote a | 544 (M + H)+ | 1.37 | 11 | a: the primary amine is prepared from the respective nitrile compound by catalytic hydrogenation using Raney-Nickel Example 7.1

7.1

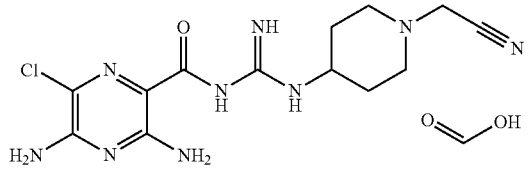

A mixture of 3,5-diamino-6-chloro-N-[(methylsulfanyl)methanimidoyl]pyrazine-2-carboxamide (Intermediate C; 0.25 g; 0.88 mmol), the primary amine (4-amino-piperidin-1-yl)acetonitrile (0.65 g; 1.06 mmol) and potassium carbonate (0.39 g; 2.82 mmol) in DMF (5 mL) is stirred at 70° C. under nitrogen atmosphere for 12 h. Water (1 mL) is added to the reaction mixture. Purification via RP HPLC (modifier: ammonium formate). The title compound is yielded as a formate salt.

Yield: 85 mg (24% of theory)

$C_{13}H_{13}ClN_9O \times CH_2O_2$ ESI Mass spectrum: m/z=352 [M+H]+

HPLC analytics: RT=6.08 min (HPLC method 7)

8. ANALYTICAL METHODS AND PREPARATIVE CHROMATOGRAPHY

As a rule, $^1$H-NMR and mass spectra have been obtained for the compounds prepared. Mass peaks given (e.g. (M+H)+, (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel made by Millipore (MATREX™, 35-70 my) is used.

Analytical HPLC/MS Methods

The HPLC retention times given are measured under the following parameters. Unless a temperature value is given, the system is run at r.t.

HPLC method 1

| Column XBridge C18, 4.6 × 30 mm, 2.5 μm (Waters) | | | | |
|---|---|---|---|---|
| Gradient time [min] | % Sol [H₂O, 0.1% TFA] | % Sol [methanol, 0.1% TFA] | Flow [mL/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4 | 60 |
| 2.35 | 0 | 100 | 4 | 60 |

HPLC method 2

| Column XBridge C18, 3 × 30 mm, 2.5 μm (Waters) | | | | |
|---|---|---|---|---|
| Gradient time [min] | % Sol [H₂O, 0.1% TFA] | % Sol [methanol] | Flow [mL/min] | Temp [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

HPLC method 3

| Gradient time [min] | % Sol [H₂O, 0.1% TFA] | % Sol [methanol] | Flow [mL/min] | Temp [° C.] |
|---|---|---|---|---|
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

Column SunFire, 3 × 30 mm, 2.5 μm (Waters)

HPLC method 4

| Gradient time [min] | % Sol [H₂O, 0.1% TFA] | % Sol [acetonitrile] | Flow [mL/min] | Temp [° C.] |
|---|---|---|---|---|
| 0.0 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Column SunFire 3 × 30 mm, 2.5 μm (Waters)

HPLC method 5

| Gradient time [min] | % Sol [H₂O, 0.1% TFA] | % Sol [methanol] | Flow [mL/min] | Temp [° C.] |
|---|---|---|---|---|
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

Column SunFire, 4.6 × 30 mm, 2.5 μm (Waters)

HPLC method 6

| Gradient time [min] | % Sol [H₂O, 0.1% TFA] | % Sol [acetonitrile] | Flow [mL/min] | Temp [° C.] |
|---|---|---|---|---|
| 0.0 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Column XBridge C18, 3 × 30 mm, 2.5 μm (Waters)

HPLC method 7

Column Synergi Hydro RP80A, 4 μm, 4.6 × 100 mm

| Gradient time [min] | % Sol [H₂O, 10% acetonitrile + 10 mM NH₄COOH] | % Sol [acetonitrile, 10% H₂O + 10 mM NH₄COOH] | Flow [mL/min] | Temp [° C.] |
|---|---|---|---|---|
| 0.0 | 100 | 0 | 1.2 | |
| 1.50 | 100 | 0 | 1.2 | |
| 11.5 | 0 | 100 | 1.2 | |
| 13.0 | 0 | 100 | 1.2 | |
| 13.50 | 100 | 0 | 1.2 | |
| 15.00 | 100 | 0 | 1.2 | |

HPLC method 8

| Gradient time [min] | % Sol [H₂O, 0.1% TFA] | % Sol [methanol] | Flow [mL/min] | Temp [° C.] |
|---|---|---|---|---|
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

Column XBridge C18, 4.6 × 30 mm, 2.5 μm (Waters)

HPLC method 9

Column: Symmetry Shield RPB, 5 μm, 4.6 × 150 mm
Mobile phase: A = H2O 90% + CH3CN 10% + HCOOH 0.1%
B = CH3CN 90% + H2O 10% + HCOOH 0.1%

| time in min | % A | % B | flow rate in ml/min |
|---|---|---|---|
| 0.00 | 95 | 5 | 1 |
| 1.50 | 95 | 5 | 1 |
| 11.05 | 5 | 95 | 1 |
| 13.00 | 5 | 95 | 1 |
| 13.03 | 95 | 5 | 1 |
| 15.00 | 95 | 5 | 1 |

HPLC method 10

Column: Synergi Hydro RP100A, 5 μm, 3.0 × 50 mm
Mobile phase: A = H2O 90% + CH3CN 10% + NH4COOH 10 mM
B = CH3CN 90% + H2O 10% + NH4COOH 10 mM

| time in min | % A | % B | flow rate in ml/min |
|---|---|---|---|
| 0.00 | 100 | 0 | 0.7 |
| 1.50 | 100 | 0 | 0.7 |
| 8.50 | 0 | 100 | 0.7 |
| 10.0 | 0 | 100 | 0.7 |
| 11.0 | 100 | 0 | 0.7 |
| 12.0 | 100 | 0 | 0.7 |

HPLC method 11

Column Simmetry Shield RPB, 5 μm, 4.6 × 150 mm

| Gradient time [min] | % Sol [H₂O, 10% acetonitrile + 0.1% HCOOH] | % Sol [acetonitrile, 10% H₂O + 0.1% HCOOH] | Flow [mL/min] | Temp [° C.] |
|---|---|---|---|---|
| 0.0 | 95 | 5 | 1.0 | |
| 1.50 | 95 | 5 | 1.0 | |
| 11.5 | 5 | 95 | 1.0 | |
| 13.0 | 5 | 95 | 1.0 | |
| 13.3 | 95 | 5 | 1.0 | |
| 15.00 | 95 | 5 | 1.0 | |

HPLC method 12

Column X-Terra ™MS C18, 2.5 μm, 4.6 × 30 mm

| Gradient time [min] | % Sol [H₂O + 0.1% formic acid] | % Sol [acetonitrile + 0.1% formic acid] | Flow [mL/min] | Temp [° C.] |
|---|---|---|---|---|
| 0.0 | 95 | 5 | 1.5 | 25° C. |
| 2.00 | 0 | 100 | 1.5 | 25° C. |
| 2.50 | 0 | 100 | 1.5 | 25° C. |
| 2.60 | 95 | 5 | 1.5 | 25° C. |

Preparative HPLC/MS Methods

The compounds are, if not stated otherwise, purified by RP-HPLC.

Columns used are Sunfire C18 or Xbridge C18 from Waters. Modifiers applied are TFA, $NH_3$ or ammonium formate as indicated.

The following abbreviations are used above and hereinafter:
ACN Acetonitrile
Alox B aluminium oxide, basic
BOC tert-Butoxycarbonyl
CDI 1,1'-Carbonyldiimidazole
DCM Methylene chloride
DIPEA Diisopropyl-ethylamine
DMAP 4-Dimethylaminopyridine
DMF N,N-Dimethylformamide
DMSO dimethyl sulfoxide
ESI Electrospray ionization
Fmoc 9H-Fluoren-9-yl-methoxycarbonyl
HATU O-(7-Azabenzotriazol-1-yl)-N,N,N',N'-tetramethyluronium hexafluorophosphate 1 M concentration of 1 mol/L
MCPBA 3-Chloroperoxybenzoic acid
MeOH methanol
Ph Phenyl
r.t. ambient temperature (about 20° C.)
TBME tert-Butylmethyl ether
TBS tert-Butyl-dimethylsilyl
TBTU 2-(1H-Benzotriazol-1-yl)-1,1,3,3-tetramethyluronium-tetrafluoroborate
TEA Triethylamine
TFA Trifluoroacetic acid
THF Tetrahydrofuran
Tr Triphenylmethyl
Xantphos 4,5-Bis(diphenylphosphino)-9,9-dimethylxanthene

arrow and asterisk indicate the binding site, i.e. the point of attachment (here: atom "A") within a chemical entity (here exemplified by the group "A-R")

9. PHARMACOLOGICAL TEST METHOD

Ussing Chamber: Mouse kidney M-1 cells were cultivated in DMEM containing 5% FCS and 5 µM dexamethasone for 10 to 12 days on polyester transwell filters. Filters were inserted into a teflon-coated well-plate which fit into the in-house ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode using an in-house built amplifier (Boehringer Ingelheim, Biberach) with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (e.g. 1-3-10 µM) to the apical solution. At the end of each experiment the amiloride sensitive I_SC was measured by adding 3 µM amiloride to the apical compartment. Results are expressed as inhibition in percent of the amiloride effect or as $IC_{50}$.

With the example compounds given above, the following $IC_{50}$ values were determined in the Ussing Chamber assay:

| | Example | | | | | | | | | | | |
|---|---|---|---|---|---|---|---|---|---|---|---|---|
| | 1.1 | 1.2 | 1.3 | 1.4 | 1.5 | 1.6 | 1.7 | 1.8 | 1.9 | 1.10 | 1.11 | 1.12 |
| $IC_{50}$ [nM] | 2 | 2 | 3 | 2 | 6 | 2 | 1 | 1 | 1 | 1 | 1 | 2 |

| | Example | | | | | | | | | | | |
|---|---|---|---|---|---|---|---|---|---|---|---|---|
| | 1.13 | 1.14 | 1.15 | 1.16 | 1.17 | 1.18 | 1.19 | 1.20 | 1.21 | 1.22 | 1.23 | 1.24 |
| $IC_{50}$ [nM] | 23 | 1 | 4 | 18 | 7 | 0.3 | 3 | 17 | 18 | 22 | 3 | 7 |

| | Example | | | | | | | | | |
|---|---|---|---|---|---|---|---|---|---|---|
| | 1.25 | 1.26 | 1.27 | 1.28 | 1.29 | 1.30 | 1.31 | 1.32 | 1.33 | 1.34 |
| $IC_{50}$ [nM] | 3 | 3 | 4 | | 8 | 2 | 2 | 13 | 5 | 4 |

| | Example | | | | | | | |
|---|---|---|---|---|---|---|---|---|
| | 2.1 | 2.2 | 2.3 | 2.4 | 3.1 | 4.1 | 4.2 | 4.3 |
| $IC_{50}$ [nM] | 38 | 31 | 47 | | 19 | 19 | 10 | 10 |

| | Example | | | | | | | | | | | |
|---|---|---|---|---|---|---|---|---|---|---|---|---|
| | 4.4 | 4.5 | 4.6 | 4.7 | 4.8 | 4.9 | 4.10 | 4.11 | 4.12 | 4.13 | 4.14 | 4.15 |
| $IC_{50}$ [nM] | 11 | 36 | 7 | 30 | 27 | 6 | 4 | 27 | 55 | 30 | 53 | 12 |

| | Example | | | | | | | | |
|---|---|---|---|---|---|---|---|---|---|
| | 4.16 | 4.17 | 4.18 | 4.19 | 4.20 | 4.21 | 4.22 | 4.23 | 4.24 |
| $IC_{50}$ [nM] | 19 | 72 | 3 | 9 | 10 | 15 | 4 | 147 | 17 |

-continued

| | Example | | | | | | | | | |
|---|---|---|---|---|---|---|---|---|---|---|
| | 5.1 | 5.2 | 5.3 | 5.4 | 6.1 | 6.2 | 6.3 | 6.4 | 6.5 | 6.6 |
| $IC_{50}$ [nM] | 266 | 80 | 169 | 176 | 5 | 27 | 1 | 3 | 6 | 1 |

| | Example | | | | | | | |
|---|---|---|---|---|---|---|---|---|
| | 6.7 | 6.8 | 6.9 | 6.10 | 6.11 | 6.12 | 6.13 | 7.1 |
| $IC_{50}$ [nM] | 3 | 5 | 8 | 3 | 3 | 2 | 3 | 35 |

10. INDICATIONS

As has been found, the compounds of formula (I) are characterised by their wide range of applications in the therapeutic field. Particular mention should be made of those applications for which the compounds according to the invention of formula (I) are preferably suited due to their pharmaceutical efficacy as ENaC inhibitors. Examples include respiratory diseases or complaints, or allergic diseases of the airways, Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or nonallergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma, particularly COPD, chronic bronchitis and asthma.

It is most preferable to use the compounds of formula (I) for the treatment of inflammatory and obstructive diseases such as COPD, chronic bronchitis, chronic sinusitis, asthma and cystic fibrosis, particularly COPD, chronic bronchitis and asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmaceutically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and
1-(2-chloro-4-hydroxyphenyl)-t-butylaminoethanole,
(−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate,
3-(4-{6-[2-Hydroxy-2-(4-hydroxy-3-hydroxymethyl-phenyl)-ethylamino]-hexyloxy}-butyl)-benzyl-sulfonamide
5-[2-(5,6-Diethyl-indan-2-ylamino)-1-hydroxy-ethyl]-8-hydroxy-1H-quinoline-2-one
4-Hydroxy-7-[2-{[2-{[3-(2-phenylethoxy)propyl]sulphonyl}ethyl]-amino}ethyl]-2(3H)-benzothiazolone
1-(2-Fluoro-4-hydroxyphenyl)-2-[4-(1-benzimidazolyl)-2-methyl-2-butylamino]ethanole
1-[3-(4-Methoxybenzyl-amino)-4-hydroxyphenyl]-2-[4-(1-benzimidazolyl)-2-methyl-2-butylamino]ethanole
1-[2H-5-hydroxy-3-oxo-4H-1,4-benzoxazin-8-yl]-2-[3-(4-N,N-dimethylaminophenyl)-2-methyl-2-propylamino]ethanole
1-[2H-5-hydroxy-3-oxo-4H-1,4-benzoxazin-8-yl]-2-[3-(4-methoxyphenyl)-2-methyl-2-propylamino]ethanole
1-[2H-5-hydroxy-3-oxo-4H-1,4-benzoxazin-8-yl]-2-[3-(4-n-butyloxyphenyl)-2-methyl-2-propylamino]ethanole
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole
5-Hydroxy-8-(1-hydroxy-2-isopropylaminobutyl)-2H-1,4-benzoxazin-3-(4H)-one
1-(4-Amino-3-chloro-5-trifluormethylphenyl)-2-tert.-butylamino)ethanole
6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-one 1-(4-Ethoxy-carbonylamino-3-cyano-5-fluorophenyl)-2-(tert.-butylamino)ethanole N-[2-Hydroxy-5-(1-hydroxy-2-{2-[4-(2-hydroxy-2-phenyl-ethylamino)-phenyl]-ethylamino}-ethyl)-phenyl]-formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxy-ethyl]-8-hydroxy-1H-quinolin-2-one

[3-(4-{6-[2-Hydroxy-2-(4-hydroxy-3-hydroxymethyl-phenyl)-ethylamino]hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenole 3-(4-{6-[2-Hydroxy-2-(4-hydroxy-3-hydroxymethyl-phenyl)-ethylamino]-hexyloxy}-butyl)-benzenesulfonamide 3-(3-{7-[2-Hydroxy-2-(4-hydroxy-3-hydroxymethyl-phenyl)-ethylamino]-heptyloxy}-propyl)-benzenesulfonamide 4-(2-{6-[4-(3-Cyclopentanesulfonyl-phenyl)-butoxy]-hexylamino}-1-hydroxy-ethyl)-2-hydroxymethyl-phenole N-Adamantan-2-yl-2-(3-{2-[2-hydroxy-2-(4-hydroxy-3-hydroxymethyl-phenyl)-ethylamino]-propyl}-phenyl)-acetamide (R,S)-4-(2-{[6-(2,2-Difluoro-4-phenylbutoxy)hexyl]amino}-1-hydroxy-ethyl)-2-(hydroxymethyl)phenole (R,S)-4-(2-{[6-(2,2-Difluoro-2-phenylethoxy)hexyl]amino}-1-hydroxy-ethyl)-2-(hydroxymethyl)phenole (R,S)-4-(2-{[4,4-Difluoro-6-(4-phenylbutoxy)hexyl]amino}-1-hydroxy-ethyl)-2-(hydroxy-methyl)phenole (R,S)-4-(2-{[6-(4,4-Difluoro-4-phenylbutoxy)hexyl]amino}-1-hydroxy-ethyl)-2-(hydroxymethyl)phenole (R,S)-5-(2-{[6-(2,2-Difluoro-2-phenylethoxy)hexyl]amino}-1-hydroxy-ethyl)-8-hydroxyquinolin-2(1H)-one (R,S)-[2-({6-[2,2-Difluoro-2-(3-methylphenyl)ethoxy]hexyl}amino)-1-hydroxyethyl]-2-(hydroxymethyl)phenole 4-(1R)-2-{[6-(2,2-Difluoro-2-phenylethoxy)hexyl]amino}-1-hydroxyethyl)-2-(hydroxymethyl)phenol (R,S)-2-(Hydroxymethyl)-4-(1-hydroxy-2-{[4,4,5I5-tetrafluoro-6-(3-phenylpropoxy)-hexyl]amino}ethyl)phenole (R,S)-[5-(2-{[6-(2,2-Difluoro-2-phenylethoxy)hexyl]amino}-1-hydroxy-ethyl)-2-hydroxy-phenyl]formamide (R,S)-4-[2-({6-[2-(3-Bromophenyl)-2,2-difluoroethoxy]hexyl}amino)-1-hydroxyethyl]-2-(hydroxymethyl)phenole (R,S)—N-[3-(1,1-Difluoro-2-{[6-({2-hydroxy-2-[4-hydroxy-3-(hydroxymethyl)phenyl]-ethyl}amino)hexyl]oxy}ethyl)phenyl]urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione (R,S)-4-[2-({6-[2,2-difluoro-2-(3-methoxyphenyl)ethoxy]hexyl}amino)-1-hydroxyethyl]-2-(hydroxymethyl)phenole 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-Difluoro-6-(4-phenylbutoxy)hexyl]amino}-1-hydroxy-ethyl)-2-(hydroxymethyl)phenole (R,S)-4-(2-{[6-(3,3-Difluoro-3-phenylpropoxy)hexyl]amino}-1-hydroxy-ethyl)-2-(hydroxymethyl)phenole (R,S)-(2-{[6-(2,2-Difluoro-2-phenylethoxy)-4,4-difluorohexyl]amino}-1-hydroxyethyl)-2-(hydroxymethyl)phenole (R,S)-4-(2-{[6-(2,2-difluoro-3-phenylpropoxy)hexyl]amino}-1-hydroxy ethyl)-2-(hydroxy-methyl)phenole 3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide 7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferably the bromide salt, Oxitropium salts, preferably the bromide salt, Flutropium salts, preferably the bromide salt, Ipratropium salts, preferably the bromide salt, Aclidinium salts, preferably the bromide salt, Glycopyrronium salts, preferably the bromide salt, Trospium salts, preferably the chloride salt, Tolterodin. From the above mentioned salts the pharmaceutically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide 2,2-Diphenylpropionic acid scopine ester-methobromide 2-Fluor-2,2-Diphenylacetic acid scopine ester-methobromide 2-Fluor-2,2-Diphenylacetic acid tropenole ester-methobromide 3,3',4,4'-Tetrafluorbenzil acid tropenole ester-methobromide 3,3',4,4'-Tetrafluorbenzil acid scopine ester-methobromide 4,4'-Difluorbenzil acid tropenole ester-methobromide 4,4'-Difluorbenzil acid scopine ester-methobromide 3,3'-Difluorbenzil acid tropenole ester-methobromide
3,3'-Difluorbenzil acid scopine ester-methobromide
9-Hydroxy-fluorene-9-carbon acid tropenole ester-methobromide
9-Fluor-fluorene-9-carbon acid tropenole ester-methobromide
9-Hydroxy-fluorene-9-carbon acid scopine ester-methobromide
9-Fluor-fluorene-9-carbon acid scopine ester methobromide
9-Methyl-fluorene-9-carbon acid tropenole estermethobromide
9-Methyl-fluorene-9-carbon acid scopine estermethobromide
Benzil acid cyclopropyl tropine ester-methobromide
2,2-Diphenylpropionic acid cyclopropyl tropine ester-methobromide
9-Hydroxy-xanthene-9-carbon acid cyclopropyl tropine ester-methobromide
9-Methyl-fluorene-9-carbon acid cyclopropyl tropine ester-methobromide
9-Methyl-xanthene-9-carbon acid cyclopropyl tropine ester-methobromide
9-Hydroxy-fluorene-9-carbon acid cyclopropyl tropine ester-methobromide
4,4'-Difluorbenzil acid methylester cyclopropyl tropine ester-methobromide
9-Hydroxy-xanthene-9-carbon acid tropenole ester-methobromide
9-Hydroxy-xanthene-9-carbon acid scopine ester methobromide
9-Methyl-xanthene-9-carbon acid tropenole ester-methobromide
9-Methyl-xanthene-9-carbon acid scopine estermethobromide
9-Ethyl-xanthene-9-carbon acid tropenole ester methobromide
9-Difluormethyl-xanthene-9-carbon acid tropenole ester-methobromide
9-Hydroxymethyl-xanthene-9-carbon acid scopine ester methobromide.

Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, and
{20R-16alpha,17alpha-[butylidenebis(oxy)]-6alpha,9alpha-difluoro-11beta-hydroxy-17beta-(methylthio)androsta-4-en-3-one},
9-fluoro-11beta,17,21-trihydroxy-16alpha-methylpregna-1,4-diene-3,20-dione 21-cyclohexanecarboxylate 17-cyclopropanecarboxylate,
16,17-butylidenedioxy-6,9-difluoro-11-hydroxy-17-(methylthio)androst-4-en-3-one
Flunisolide-21-[4'-(nitrooxymethyl)benzoate]
6,9-Difluoro-17-[(2-furanylcarbonyl)oxy]-11-hydroxy-16-methyl-3-oxo-androsta-1,4-dien-17-carbothion acid (S)-fluoromethylester,
6,9-Difluoro-11-hydroxy-16-methyl-3-oxo-17-propionyloxy-androsta-1,4-dien-17-carbothion acid (S)-(2-oxo-tetrahydro-furan-3S-yl)ester, and
6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester
optionally in racemic form, as enantiomers, diastereomeres or as pharmaceutically acceptable salts, solvates or hydrates.

Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and
5-[(N-(2,5-dichloro-3-pyridinyl)-carboxamide]-8-methoxyquinoline
5-[N-(3,5-dichloro-1-oxido-4-pyridinyl)-carboxamide]-8-methoxy-2-(trifluoromethyl)-quinoline
N-(3,5-dichloropyrid-4-yl)-[1-(4-fluorobenzyl)-5-hydroxyindole-3-yl]glyoxyl acid amide), 9-[(2-fluorophenyl)methyl]-N-methyl-2-(trifluoromethyl)-9H-purine-6-amine
4-[(2R)-2-[3-(cyclopentyloxy)-4-methoxyphenyl]-2-phenylethyl]-pyridine,
N-[(3R)-3,4,6,7-tetrahydro-9-methyl-4-oxo-1-phenylpyrrolo[3,2,1-jk][1,4]benzodiazepin-3-yl]-4-Pyridinecarboxamide,
4-[6,7-diethoxy-2,3-bis(hydroxymethyl)-1-naphthalenyl]-1-(2-methoxyethyl)-2(1H)-pyridinone,
2-[4-[6,7-diethoxy-2,3-bis(hydroxymethyl)-1-naphthalenyl]-2-pyridinyl]-4-(3-pyridinyl)-1 (2H)-Phthalazinone,
(3-(3-cyclopenyloxy-4-methoxybenzyl)-6-ethylamino-8-isopropyl-3H-purine,
beta-[3-(cyclopentyloxy)-4-methoxyphenyl]-1,3-dihydro-1,3-dioxo-2H-isoindole-2-propanamide,
9-ethyl-2-methoxy-7-methyl-5-propyl-imidazo[1,5-a]pyrido[3,2-e]pyrazin-6(5H)-one
5-[3-(cyclopentyloxy)-4-methoxyphenyl]-3-[(3-methylphenyl)methyl](3S,5S)-2-piperidinone,
4-[1-[3,4-bis(difluoromethoxy)phenyl]-2-(3-methyl-1-oxido-4-pyridinyl)ethyl]-alpha,alpha-bis(trifluoromethyl)-Benzenemethanol
N-(3,5-Dichloro-1-oxo-pyridine-4-yl)-4-difluoromethoxy-3-cyclopropylmethoxybenzamide
(−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide
(R)-(+)-1-(4-Bromobenzyl)-4-[(3-cyclopentyloxy)-4-methoxyphenyl]-2-pyrrolidone
3-(Cyclopentyloxy-4-methoxyphenyl)-1-(4-N'-[N-2-cyano-S-methyl-isothioureido]benzyl)-2-pyrrolidone
cis[4-Cyano-4-(3-cyclopentyloxy-4-methoxyphenyl)cyclohexan-1-carbon acid]
2-carbomethoxy-4-cyano-4-(3-cyclopropylmethoxy-4-difluoromethoxyphenyl)cyclohexan-1-one
cis[4-Cyano-4-(3-cyclopropylmethoxy-4-difluoromethoxyphenyl)cyclohexan-1-ol]
(R)-(+)-Ethyl[4-(3-cyclopentyloxy-4-methoxyphenyl)pyrrolidine-2-yliden]acetate
(S)-(−)-Ethyl[4-(3-cyclopentyloxy-4-methoxyphenyl)pyrrolidine-2-yliden]acetate
9-Cyclopentyl-5,6-dihydro-7-ethyl-3-(2-thienyl)-9H-pyrazolo[3,4-c]-1,2,4-triazolo[4,3-a]pyridine
9-Cyclopentyl-5,6-dihydro-7-ethyl-3-(tert-butyl)-9H-pyrazolo[3,4-c]-1,2,4-triazolo[4,3-a]pyridine
optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukast, Pranlukast, Zafirlukast, Masikulast, L-733321 (see compound 2ab of D. Guay et al, Bioorg. Med. Chem. Lett. 8 (1998) 453-458) and (E)-8-[2-[4-[4-(4-Fluorophenyl)butoxy]phenyl]ethenyl]-2-(1H-tetrazole-5-yl)-4H-1-benzopyran-4-one (MEN-91507)

4-[6-Acetyl-3-[3-(4-acetyl-3-hydroxy-2-propylphenylthio) propoxy]-2-propylphenoxy]-butyric acid (MN-001)

1-(((R)-3-(2-(6,7-Difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid

[2-[[2-(4-tert-Butyl-2-thiazolyl)-5-benzofuranyl]oxymethyl]phenyl]acetic acid optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximab, Trastuzumab, Panitumumab Gefitinib, Canertinib, Erlotinib, Mab ICR-62 and 4-[(3-Chlor-4-fluorophenyl)amino]-6-{[4-(morpholine-4-yl)-1-oxo-2-butene-1-yl]amino}-7-cyclopropylmethoxy-quinazoline 4-[(3-Chlor-4-fluorophenyl)amino]-6-{[4-(N,N-diethylamino)-1-oxo-2-butene-1-yl]amino}-7-cyclopropylmethoxy-quinazoline 4-[(3-Chlor-4-fluorophenyl)amino]-6-{[4-(N,N-dimethylamino)-1-oxo-2-butene-1-yl]amino}-7-cyclopropylmethoxy-quinazoline 4-[(R)-(1-Phenyl-ethyl)amino]-6-{[4-(morpholine-4-yl)-1-oxo-2-butene-1-yl]amino}-7-cyclopentyloxy-quinazoline 4-[(3-Chlor-4-fluorophenyl)amino]-6-{[4-((R)-6-methyl-2-oxo-morpholine-4-yl)-1-oxo-2-butene-1-yl]amino}-7-cyclopropylmethoxy-quinazoline 4-[(3-Chlor-4-fluorophenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline 4-[(3-Chlor-4-fluorophenyl)amino]-6-{[4-((R)-2-methoxymethyl-6-oxo-morpholine-4-yl)-1-oxo-2-butene-1-yl]amino}-7-cyclopropylmethoxy-quinazoline 4-[(3-Chlor-4-fluorophenyl)amino]-6-[2-((S)-6-methyl-2-oxo-morpholine-4-yl)-ethoxy]-7-methoxy-quinazoline 4-[(3-Chlor-4-fluorophenyl)amino]-6-({4-[N-(2-methoxyethyl)-N-methyl-amino]-1-oxo-2-butene-1-yl}amino)-7-cyclopropylmethoxy-quinazoline 4-[(3-Chlor-4-fluorophenyl)amino]-6-{[4-(N,N-dimethylamino)-1-oxo-2-butene-1-yl]amino}-7-cyclopentyloxy-quinazoline 4-[(R)-(1-Phenyl-ethyl)amino]-6-{[4-(N,N-bis-(2-methoxyethyl)-amino)-1-oxo-2-butene-1-yl]amino}-7-cyclopropylmethoxy-quinazoline 4-[(R)-(1-Phenyl-ethyl)amino]-6-({4-[N-(2-methoxyethyl)-N-ethyl-amino]-1-oxo-2-butene-1-yl}amino)-7-cyclopropylmethoxy-quinazoline 4-[(R)-(1-Phenyl-ethyl)amino]-6-({4-[N-(2-methoxyethyl)-N-methyl-amino]-1-oxo-2-butene-1-yl}amino)-7-cyclopropylmethoxy-quinazoline 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline 4-[(3-Chlor-4-fluorophenyl)amino]-6-{[4-(N,N-dimethylamino)-1-oxo-2-butene-1-yl]amino}-7-((R)-tetrahydrofuran-3-yloxy)-quinazoline 4-[(3-Chlor-4-fluorophenyl)amino]-6-{[4-(N,N-dimethylamino)-1-oxo-2-butene-1-yl]amino}-7-((S)-tetrahydrofuran-3-yloxy)-quinazoline 4-[(3-Chlor-4-fluorophenyl)amino]-6-({4-[N-(2-methoxyethyl)-N-methyl-amino]-1-oxo-2-butene-1-yl}amino)-7-cyclopentyloxy-quinazoline 4-[(3-Chlor-4-fluorophenyl)amino]-6-{[4-(N-cyclopropyl-N-methyl-amino)-1-oxo-2-butene-1-yl]amino}-7-cyclopentyloxy-quinazoline 4-[(3-Chlor-4-fluorophenyl)amino]-6-{[4-(N,N-dimethylamino)-1-oxo-2-butene-1-yl]amino}-7-[(R)-(tetrahydrofuran-2-yl)methoxy]-quinazoline 4-[(3-Chlor-4-fluorophenyl)amino]-6-{[4-(N,N-dimethylamino)-1-oxo-2-butene-1-yl]amino}-7-[(S)-(tetrahydrofuran-2-yl)methoxy]-quinazoline 4-[(3-Ethinyl-phenyl)amino]-6,7-bis-(2-methoxy-ethoxy)-quinazoline 4-[(3-Chlor-4-fluorophenyl)amino]-7-[3-(morpholine-4-yl)-propyloxy]-6-[(vinylcarbonyl)amino]-quinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorophenyl)amino]-6-{[4-(N,N-dimethylamino)-1-oxo-2-butene-1-yl]amino}-7-ethoxy-quinoline 4-{[3-Chlor-4-(3-fluor-benzyloxy)-phenyl]amino}-6-(5-{[(2-methansulfonyl-ethyl)amino]methyl}-furan-2-yl) quinazoline 4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorophenyl)amino]-6-{[4-(morpholine-4-yl)-1-oxo-2-butene-1-yl]amino}-7-[(tetrahydrofuran-2-yl)methoxy]-quinazoline 4-[(3-Chlor-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-butene-1-yl]amino}-quinazoline 4-[(3-Chlor-4-fluorophenyl)amino]-6-[2-(2,2-dimethyl-6-oxo-morpholine-4-yl)-ethoxy]-7-methoxy-quinazoline 4-[(3-Chlor-4-fluorophenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluorophenyl)amino]-7-[2-(2,2-dimethyl-6-oxo-morpholine-4-yl)-ethoxy]-6-[(S)-(tetrahydrofuran-2-yl)methoxy]-quinazoline 4-[(3-Chlor-4-fluorophenyl)amino]-6-{2-[4-(2-oxo-morpholine-4-yl)-piperidin-1-yl]-ethoxy}-7-methoxy-quinazoline 4-[(3-Chlor-4-fluorophenyl)amino]-6-[1-(tert.-butyloxycarbonyl)-piperidine-4-yloxy]-7-methoxy-quinazoline 4-[(3-Chlor-4-fluorophenyl)amino]-6-(trans-4-amino-cyclohexane-1-yloxy)-7-methoxy-quinazoline 4-[(3-Chlor-4-fluorophenyl)amino]-6-(trans-4-methansulfonylamino-cyclohexane-1-yloxy)-7-methoxy-quinazoline 4-[(3-Chlor-4-fluorophenyl)amino]-6-(tetrahydropyran-3-yloxy)-7-methoxy-quinazoline 4-[(3-Chlor-4-fluorophenyl)amino]-6-(1-methyl-piperidine-4-yloxy)-7-methoxy-quinazoline
4-[(3-Chlor-4-fluorophenyl)amino]-6-{1-[(morpholine-4-yl)carbonyl]-piperidine-4-yloxy}-7-methoxy-quinazoline
4-[(3-Chlor-4-fluorophenyl)amino]-6-{1-[(methoxymethyl)carbonyl]-piperidine-4-yloxy}-7-methoxy-quinazoline
4-[(3-Chlor-4-fluorophenyl)amino]-6-(piperidine-3-yloxy)-7-methoxy-quinazoline
4-[(3-Chlor-4-fluorophenyl)amino]-6-[1-(2-acetylamino-ethyl)-piperidine-4-yloxy]-7-methoxy-quinazoline
4-[(3-Chlor-4-fluorophenyl)amino]-6-(tetrahydropyran-4-yloxy)-7-ethoxy-quinazoline
4-[(3-Chlor-4-fluorophenyl)amino]-6-((S)-tetrahydrofuran-3-yloxy)-7-hydroxy-quinazoline
4-[(3-Chlor-4-fluorophenyl)amino]-6-(tetrahydropyran-4-yloxy)-7-(2-methoxy-ethoxy)-quinazoline
4-[(3-Chlor-4-fluorophenyl)amino]-6-{trans-4-[(dimethylamino)sulfonylamino]-cyclohexane-1-yloxy}-7-methoxy-quinazoline
4-[(3-Chlor-4-fluorophenyl)amino]-6-{trans-4-[(morpholine-4-yl)carbonylamino]-cyclohexane-1-yloxy}-7-methoxy-quinazoline
4-[(3-Chlor-4-fluorophenyl)amino]-6-{trans-4-[(morpholine-4-yl)sulfonylamino]-cyclohexane-1-yloxy}-7-methoxy-quinazoline
4-[(3-Chlor-4-fluorophenyl)amino]-6-(tetrahydropyran-4-yloxy)-7-(2-acetylamino-ethoxy)-quinazoline
4-[(3-Chlor-4-fluorophenyl)amino]-6-(tetrahydropyran-4-yloxy)-7-(2-methansulfonylamino-ethoxy)-quinazoline
4-[(3-Chlor-4-fluorophenyl)amino]-6-{1-[(piperidine-1-yl)carbonyl]-piperidine-4-yloxy}-7-methoxy-quinazoline
4-[(3-Chlor-4-fluorophenyl)amino]-6-(1-aminocarbonylmethyl-piperidine-4-yloxy)-7-methoxy-quinazoline
4-[(3-Chlor-4-fluorophenyl)amino]-6-(cis-4-{N-[(tetrahydropyran-4-yl)carbonyl]-N-methyl-amino}-cyclohexane-1-yloxy)-7-methoxy quinazoline
4-[(3-Chlor-4-fluorophenyl)amino]-6-(cis-4-{N-[(morpholine-4-yl)carbonyl]-N-methyl-amino}-cyclohexane-1-yloxy)-7-methoxy-quinazoline
4-[(3-Chlor-4-fluorophenyl)amino]-6-(cis-4-{N-[(morpholine-4-yl)sulfonyl]-N-methyl-amino}-cyclohexane-1-yloxy)-7-methoxy-quinazoline
4-[(3-Chlor-4-fluorophenyl)amino]-6-(trans-4-ethansulfonylamino-cyclohexane-1-yloxy)-7-methoxy-quinazoline
4-[(3-Chlor-4-fluorophenyl)amino]-6-(1-methansulfonyl-piperidine-4-yloxy)-7-ethoxy-quinazoline
4-[(3-Chlor-4-fluorophenyl)amino]-6-(1-methansulfonyl-piperidine-4-yloxy)-7-(2-methoxy-ethoxy)-quinazoline
4-[(3-Chlor-4-fluorophenyl)amino]-6-[1-(2-methoxy-acetyl)-piperidine-4-yloxy]-7-(2-methoxy-ethoxy)-quinazoline
4-[(3-Chlor-4-fluorophenyl)amino]-6-(cis-4-acetylamino-cyclohexane-1-yloxy)-7-methoxy-quinazoline
4-[(3-Ethinyl-phenyl)amino]-6-[1-(tert-butyloxycarbonyl)-piperidine-4-yloxy]-7-methoxy-quinazoline
4-[(3-Ethinyl-phenyl)amino]-6-(tetrahydropyran-4-yloxy]-7-methoxy-quinazoline
4-[(3-Chlor-4-fluorophenyl)amino]-6-(cis-4-{N-[(piperidine-1-yl)carbonyl]-N-methyl-amino}-cyclohexane-1-yloxy)-7-methoxy-quinazoline
4-[(3-Chlor-4-fluorophenyl)amino]-6-(cis-4-{N-[(4-methyl-piperazine-1-yl)carbonyl]-N-methyl-amino}-cyclohexane-1-yloxy)-7-methoxy-quinazoline
4-[(3-Chlor-4-fluorophenyl)amino]-6-{cis-4-[(morpholine-4-yl)carbonylamino]-cyclohexane-1-yloxy}-7-methoxy-quinazoline
4-[(3-Chlor-4-fluorophenyl)amino]-6-{1-[2-(2-oxopyrrolidine-1-yl)ethyl]-piperidine-4-yloxy}-7-methoxy-quinazoline
4-[(3-Chlor-4-fluorophenyl)amino]-6-{1-[(morpholine-4-yl)carbonyl]-piperidine-4-yloxy}-7-(2-methoxy-ethoxy)-quinazoline
4-[(3-Ethinyl-phenyl)amino]-6-(1-acetyl-piperidine-4-yloxy)-7-methoxy-quinazoline
4-[(3-Ethinyl-phenyl)amino]-6-(1-methyl-piperidine-4-yloxy)-7-methoxy-quinazoline
4-[(3-Ethinyl-phenyl)amino]-6-(1-methansulfonyl-piperidine-4-yloxy)-7-methoxy-quinazoline
4-[(3-Chlor-4-fluorophenyl)amino]-6-(1-methyl-piperidine-4-yloxy)-7-(2-methoxy-ethoxy)-quinazoline
4-[(3-Chlor-4-fluorophenyl)amino]-6-(1-isopropyloxycarbonyl-piperidine-4-yloxy)-7-methoxy-quinazoline
4-[(3-Chlor-4-fluorophenyl)amino]-6-(cis-4-methylamino-cyclohexane-1-yloxy)-7-methoxy-chinazoline
4-[(3-Chlor-4-fluorophenyl)amino]-6-{cis-4-[N-(2-methoxy-acetyl)-N-methyl-amino]-cyclohexane-1-yloxy}-7-methoxy-quinazoline
4-[(3-Ethinyl-phenyl)amino]-6-(piperidine-4-yloxy)-7-methoxy-quinazoline
4-[(3-Ethinyl-phenyl)amino]-6-[1-(2-methoxy-acetyl)-piperidine-4-yloxy]-7-methoxy-quinazoline
4-[(3-Ethinyl-phenyl)amino]-6-{1-[(morpholine-4-yl)carbonyl]-piperidine-4-yloxy}-7-methoxy-quinazoline
4-[(3-Chlor-4-fluorophenyl)amino]-6-{1-[cis-2,6-dimethyl-morpholine-4-yl)carbonyl]-piperidine-4-yloxy}-7-methoxy-quinazoline
4-[(3-Chlor-4-fluorophenyl)amino]-6-{1-[(2-methyl-morpholine-4-yl)carbonyl]-piperidine-4-yloxy}-7-methoxy-quinazoline
4-[(3-Chlor-4-fluorophenyl)amino]-6-{1-[(S,S)-(2-oxa-5-aza-bicyclo[2.2.1]hept-5-yl)carbonyl]-piperidine-4-yloxy}-7-methoxy-quinazoline
4-[(3-Chlor-4-fluorophenyl)amino]-6-{1-[(N-methyl-N-2-methoxyethyl-amino)carbonyl]-piperidine-4-yloxy}-7-methoxy-quinazoline
4-[(3-Chlor-4-fluorophenyl)amino]-6-(1-ethyl-piperidine-4-yloxy)-7-methoxy-quinazoline
4-[(3-Chlor-4-fluorophenyl)amino]-6-{1-[(2-methoxyethyl)carbonyl]-piperidine-4-yloxy}-7-methoxy-quinazoline
4-[(3-Chlor-4-fluorophenyl)amino]-6-{1-[(3-methoxypropyl-amino)-carbonyl]-piperidine-4-yloxy}-7-methoxy-quinazoline
4-[(3-Chlor-4-fluorophenyl)amino]-6-[cis-4-(N-methansulfonyl-N-methyl-amino)-cyclohexane-1-yloxy]-7-methoxy-quinazoline
4-[(3-Chlor-4-fluorophenyl)amino]-6-[cis-4-(N-acetyl-N-methyl-amino)-cyclohexane-1-yloxy]-7-methoxy-quinazoline
4-[(3-Chlor-4-fluorophenyl)amino]-6-(trans-4-methylamino-cyclohexane-1-yloxy)-7-methoxy-quinazoline
4-[(3-Chlor-4-fluorophenyl)amino]-6-[trans-4-(N-methansulfonyl-N-methyl-amino)-cyclohexane-1-yloxy]-7-methoxy-quinazoline
4-[(3-Chlor-4-fluorophenyl)amino]-6-(trans-4-dimethylamino-cyclohexane-1-yloxy)-7-methoxy-quinazoline
4-[(3-Chlor-4-fluorophenyl)amino]-6-(trans-4-{N-[(morpholine-4-yl)carbonyl]-N-methyl-amino}-cyclohexane-1-yloxy)-7-methoxy-quinazoline
4-[(3-Chlor-4-fluorophenyl)amino]-6-[2-(2,2-dimethyl-6-oxo-morpholine-4-yl)-ethoxy]-7-[(S)-(tetrahydrofuran-2-yl)methoxy]-quinazoline
4-[(3-Chlor-4-fluorophenyl)amino]-6-(1-methansulfonyl-piperidine-4-yloxy)-7-methoxy-quinazoline 4-[(3-Chlor-4-fluorophenyl)amino]-6-(1-cyano-piperidine-4-yloxy)-7-methoxy-quinazoline optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred dopamine antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmaceutically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmaceutically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred PAF antagonists which may be mentioned include Lexipafante and
4-(2-Chlorphenyl)-9-methyl-2-[3(4-morpholinyl)-3-propanone-1-yl]-6H-thieno-[3,2-f]-[1,2,4]triazolo[4,3-a][1,4]diazepine
6-(2-Chlorphenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine
optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinyl)ethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409), optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MRP4-Inhibitors which may be mentioned include N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-S-glutathione, Estradiol 17-beta-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, (E)-3-[[[3-[2-(7-Chloro-2-quinolinyl)ethenyl]phenyl]-[3-dimethylamino)-3-oxopropyl]thio]methyl]thio]-propanoic acid alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast and Dipyridamol, optionally in racemic form, as enantiomers, diastereomers or as pharmaceutically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred iNOS-Inhibitors which may be mentioned include S-(2-Aminoethyl)isothio-urea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA ($N^\omega$-Nitro-L-arginin), L-NAME ($N^\omega$-Nitro-L-argininmethylester), L-NMMA ($N^\omega$-Monomethyl-L-arginin), L-NIO ($N^\omega$-Iminoethyl-L-ornithin), L-NIL ($N^\omega$-iminoethyl-lysin), (S)-6-Acetimidoylamino-2-aminohexanoic acid (1H-tetrazole-5-yl)-amide N-[[3-(aminomethyl)phenyl]methyl]-ethanimidamide, (S)-4-(2-acetimidoylamino-ethylsulfanyl)-2-amino-buturic acid, 2-[2-(4-Methoxy-pyridine-2-yl)-ethyl]-3H-imidazo[4,5-b]pyridine, 2-((R)-3-amino-1-phenyl-propoxy)-4-chlor-5-fluorbenzonitrile, 2-((1R,3S)-3-amino-4-hydroxy-1-thiazole-5-yl-butylsulfanyl)-6-trifluoromethyl-nicotinonitrile, 2-((1R,3S)-3-amino-4-hydroxy-1-thiazole-5-yl-butylsulfanyl)-4-chlor-benzonitrile, 2-((1R,3S)-3-amino-4-hydroxy-1-thiazole-5-yl-butylsulfanyl)-5-chlor-benzonitrile, (2S,4R)-2-amino-4-(2-chlor-5-trifluoromethyl-phenylsulfanyl)-4-thiazole-5-yl-butane-1-ol, 2-((1R,3S)-3-amino-4-hydroxy-1-thiazole-5-yl-butylsulfanyl)-5-chlor-nicotinonitrile, 4-((S)-3-amino-4-hydroxy-1-phenyl-butylsulfanyl)-6-methoxy-nicotinonitrile and substituted 3-phenyl-3,4-dihydro-1-isoquinolinamine as for instance 1S,5S,6R)-7-Chlor-5-methyl-2-aza-bicyclo[4.1.0]hept-2-ene-3-ylamin(4R,5R)-5-Ethyl-4-methyl-thiazolidine-2-ylideneamine, (1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethylphenoxy)-ethoxy]-2-phenyl-pyridine, 3-{[(Benzo[1,3] dioxol-5-ylmethyl)-carbamoyl]-methyl}-4-(2-imidazole-1-yl-pyrimidine-4-yl)-piperazine-1-carbon acid methylester, (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Further examples of preferred iNOS-Inhibitors which may be mentioned include antisense-Oligonucleotide, especially those antisense-Oligonucleotide bindung iNOS-coding nucleinic acids, examples therefore are disclosed in WO 01/52902.

Examples of preferred SYK-inhibitors which may be mentioned include
2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propanediamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propanediamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenyl)methyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamin,
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;

1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;
[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred corrections of the cystic fibrosis transmembrane regulator (CFTR) and CFTR potentiators which may be mentioned include, preferably VX-770 and VX-809

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmaceutically acceptable substance which is not an active substance but which can be formulated with the active substance or substances in the pharmaceutically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmaceutically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation 1 capsule contains:

| active substance | 0.5 mg |
|---|---|
| lactose for inhalation | 5.0 mg |
| | 5.5 mg |

Preparation:
The active substance is mixed with lactose for inhalation. The mixture is packed into capsules in a capsule-making machine (weight of the empty capsule approx. 50 mg).

| weight of capsule: | 55.5 mg |
|---|---|
| size of capsule = | 3 |

The invention claimed is:
1. A compound of formula (I),

(I)

characterized in that
X denotes Cl or Br,
$R^1$ denotes H or methyl,
m and n denote 1,
$R^2$ denotes H or is selected from the group consisting of methyl, —C(O)O$R^{2.1}$ and —C(O)N$R^{2.2}R^{2.3}$,
  wherein,
  $R^{2.1}$ denotes H or is selected from the group consisting of optionally substituted $C_{1-8}$-alkyl-, optionally substituted $C_{3-8}$-cycloalkyl- and optionally substituted phenyl-$C_{1-4}$-alkyl-,
  $R^{2.2}$, $R^{2.3}$ independently from each other denote H or are selected from the group consisting of optionally substituted $C_{1-8}$-alkyl-, optionally substituted $C_{3-8}$-cycloalkyl- and optionally substituted —$C_{1-4}$-alkyl-$C_{6-10}$-aryl,
$R^3$ denotes H or is selected from the group consisting of
  —CN, —$C_{1-4}$-alkyl-non aromatic heterocycle, —$CH_2$—O—($C_2H_4$—O)$_q$—$CH_3$, —$CH_2$—O—($C_2H_4$—O)$_q$—H, —PO(O$R^{3.4}$)(O—$R^{3.5}$), —$C_{1-4}$-alkyl-S(O)$_2$OH, —$C_{1-4}$-alkyl-S(O)$_r$—$C_{1-6}$-alkyl, —$C_{1-4}$-alkyl-COOH, —$C_{1-4}$-alkyl-C(O)O$R^{3.8}$,
  $C_{1-8}$-alkyl, optionally substituted $C_{3-8}$-cycloalkyl-, $R^{3.1}$—OC(O)—, $R^{3.2}$N($R^{3.3}$)C(O)—, optionally substituted C-linked-nonaromatic heterocycle-$C_{1-3}$-alkyl, and —($CH_2$)$_p$—N$R^{3.6}R^{3.7}$,
  wherein,
  p is 1, 2, 3 or 4,
  q is 1, 2, 3 or 4,
  r is 0, 1 or 2,
  $R^{3.1}$ is selected from the group consisting of H, optionally substituted $C_{1-8}$-alkyl-, optionally substituted $C_{3-8}$-cycloalkyl-, hydroxyethoxy-$C_{2-4}$-alkyl-, methoxyethoxy-$C_{2-4}$-alkyl-, —$C_{1-4}$-alkyl-S(O)$_s$—$C_{1-4}$-alkyl, optionally substituted phenyl-$C_{1-2}$-alkyl-, optionally substituted heteroaryl-$C_{1-2}$-alkyl-, C-linked 5-7-membered nonaromatic heterocycle, and 5-7-membered nonaromatic heterocycle-$C_{1-4}$-alkyl-
  $R^{3.1}$, $R^{3.3}$ independently from each other denote H or are selected from the group consisting of optionally substituted $C_{1-8}$-alkyl-, optionally substituted $C_{3-8}$-cycloalkyl-, —$C_{2-8}$-alkyl-O—$C_{1-4}$-alkyl, hydroxy-$C_{2-4}$-alkyl-, methoxyethoxy-$C_{2-4}$-alkyl-, —$C_{1-8}$-alkyl-S(O)$_s$—$C_{1-6}$-alkyl, —$CH_2$—COOH, —$CH_2$—COO—$C_{1-4}$-alkyl, —$CH_2$—CO—NH—$C_{1-4}$-alkyl, —$C_{1-4}$-alkyl-5-to 7-membered nonaromatic heterocycle-$R^{3.3.3}$, —$C_{1-4}$-alkyl-5-to 7-membered heteroaryl-$R^{3.3.4}$, -5- to 8-membered nonaromatic heterocycle-$R^{3.3.5}$, -5-to 7-membered heteroaryl-$R^{3.3.6}$,
  optionally substituted —$C_{1-4}$-alkyl-phenyl-$R^{3.3.1}$ and optionally substituted -phenyl-$R^{3.3.2}$,
  wherein
  s is 0, 1 or 2
  $R^{3.3.1}$ denotes H or is selected from the group consisting of
    —COOH, —COO—$C_{1-4}$-alkyl, —O—$C_{1-4}$-alkyl, —S—$CF_3$, —$SO_2$—$C_{1-3}$-alkyl, —$SO_2$—$NH_2$, —$CONH_2$, optionally substituted 5-to 7-membered nonaromatic heterocycle- and -5-to 7-membered nonaromatic heterocycle-$C_{1-3}$-alkyl,
  $R^{3.3.2}$ denotes H or is selected from the group consisting of
    —CO—N($C_{1-3}$-alkyl)nonaromatic heterocycle-$C_{1-4}$-alkyl, —N($SO_2$—$C_{1-3}$-alkyl)($CH_2CONH$ $C_{1-3}$-alkyl), —N(CO $C_{1-3}$-alkyl)($C_{1-4}$-alkyl-N($C_{1-3}$-alkyl)$_2$),
    —N($C_{1-3}$-alkyl)CO—$C_{1-4}$-alkyl-N($C_{1-3}$-alkyl)$_2$, —$C_{1-3}$-alkyl-nonaromatic heterocycle,
    —$SO_2$—N($C_{1-3}$-alkyl)$C_{1-4}$-alkyl-N($C_{1-3}$-alkyl)$_2$, —$SO_2NH_2$, —$SO_2OH$, —COOH, —COO—$C_{1-3}$-alkyl, —$CONH_2$, —CONH—$C_{1-3}$-alkyl-N($C_{1-3}$-alkyl)$_2$, —O—$C_{2-3}$-alkyl-N($C_{1-3}$-alkyl)$_2$, —N($SO_2CH_3$)—$C_{1-3}$-alkyl-N($C_{1-3}$-alkyl)$_2$, and —$C_{1-3}$-alkyl-N($R^{3.3.3.1}$)$R^{3.3.2.2}$,
    wherein,
    $R^{3.3.2.1}$ denotes H, $C_{1-4}$-alkyl-, $C_{1-4}$-alkyl-CO— or $C_{1-4}$-alkyl-$SO_2$—,
    $R^{3.3.2.2}$ denotes H or $C_{1-4}$-alkyl-, or
    $R^{3.3.2.1}$ and $R^{3.3.2.2}$ together with the nitrogen atom they are attached to form an optionally substituted 4-7-membered heterocycle containing at least one N-atom,
  $R^{3.3.3}$ denotes H or $C_{1-3}$-alkyl,
  $R^{3.3.4}$ denotes H or $C_{1-3}$-alkyl,
  $R^{3.3.5}$ denotes H, $C_{1-3}$-alkyl, oxo or —$C_{1-3}$-alkyl-COO—$C_{1-3}$-alkyl,
  $R^{3.3.6}$ denotes H, oxo, $C_{1-3}$-alkyl or —$C_{1-3}$-alkyl-COO—$C_{1-3}$-alkyl,
  $R^{3.2}$ and $R^{3.3}$ together with the nitrogen atom they are attached to form an optionally substituted 5- to 7-membered heterocycle,
  $R^{3.4}$, $R^{3.5}$ independently from each other denote H or $C_{1-4}$-alkyl,
  $R^{3.6}$ denotes H, $C_{1-4}$-alkyl-, $C_1$-$C_4$-alkyl—CO— or $C_{1-4}$-alkyl-$SO_2$—
  $R^{3.7}$ denotes H or $C_{1-4}$-alkyl-, or
  $R^{3.6}$ and $R^{3.7}$ together with the nitrogen atom they are attached to form an optionally substituted 4-7-membered heterocycle containing at least one N-atom,
  $R^{3.8}$ denotes H or is selected from the group consisting of optionally substituted $C_{1-8}$-alkyl-, optionally substituted $C_{3-8}$-cycloalkyl- and optionally substituted phenyl-$C_{1-4}$-alkyl-,
or tautomers or optionally the pharmaceutically acceptable acid addition salts thereof.

2. The compound of formula (I) according to claim 1, characterized in that

X denotes Cl or Br, $R^1$ denotes H, $R^2$ denotes H or is selected from the group consisting of methyl, —C(O)O$R^{2.1}$ and —C(O)N$R^{2.2}R^{2.3}$ wherein, $R^{2.1}$ denotes $C_{1-3}$-alkyl-, $R^{2.2}$, $R^{2.3}$ independently from each other denote H or phenyl-$C_{1-4}$-alkyl-, $R^3$ is selected from the group consisting of
—CN, —CH$_2$-morpholinyl, —CH$_2$—O—(C$_2$H$_4$—O)$_3$—CH$_3$, —PO(O—$R^{3.4}$)(O—$R^{3.5}$), —$C_{1-3}$-alkyl-S(O)$_2$OH, —$C_{1-3}$-alkyl, —$C_{1-3}$-alkyl-COOH, —$C_{1-3}$-alkyl-COOCH$_3$, $C_{3-8}$-cycloalkyl-, $R^{3.1}$—OC(O)—, $R^{3.2}$N($R^{3.3}$)C(O)— and —C-linked nonaromatic heterocycle-$R^{3.3.6}$, wherein r is 0, 1 or 2, $R^{3.1}$ denotes H, $C_{1-8}$-alkyl- or phenyl-$C_{1-2}$-alkyl-, $R^{3.2}$, $R^{3.3}$ independently from each other denote H or are selected from the group consisting of $C_{1-8}$-alkyl-, $C_{3-8}$-cycloalkyl-, —$C_{2-8}$-alkyl-O—$C_{1-4}$-alkyl, —$C_{1-8}$-alkyl-S—$C_{1-4}$-alkyl, —$C_{1-4}$-alkyl-S(O)$_s$—$C_{2-6}$-alkyl, —CH$_2$—COOH, —CH$_2$—COO—$C_{1-4}$-alkyl, —CH$_2$—CO—NH—$C_{1-4}$-alkyl, optionally substituted —CH$_2$-phenyl-$R^{3.3.1}$, optionally substituted -phenyl-$R^{3.3.2}$, —$C_{1-4}$-alkyl-5- to 7-membered nonaromatic heterocycle-$R^{3.3.3}$, —$C_{1-4}$-alkyl-5-to 7-membered heteroaryl-$R^{3.3.4}$, -5-to 8-membered nonaromatic heterocycle-$R^{3.3.5}$, and -5-to 7-membered heteroaryl-$R^{3.3.6}$, wherein s is 0, 1 or 2, $R^{3.3.1}$ denotes H or is selected from the group consisting of —SO$_2$—$C_{1-3}$-alkyl, —SO$_2$—NH$_2$, —CONH$_2$, -5-to 7-membered nonaromatic heterocycle-$R^{3.3.7}$, -OMe, —S—CF$_3$ and —COO—$C_{1-4}$-alkyl, $R^{3.3.2}$ denotes H or is selected from the group consisting of
—CO—N(CH$_3$)(nonaromatic heterocycle-$C_{1-4}$-alkyl), —N(SO$_2$—CH$_3$)(CH$_2$CONHCH$_3$), —N(COCH$_3$)($C_{1-4}$-alkyl-N(CH$_3$)$_2$), —N(CH$_3$)CO $C_{1-4}$-alkyl-N(CH$_3$)$_2$, —$C_{1-3}$-alkyl-nonaromatic heterocycle, —SO$_2$—N(CH$_3$)($C_{1-3}$-alkyl-N(CH$_3$)$_2$), —SO$_2$NH$_2$, —SO$_2$OH,
—COOH, —COO—$C_{1-3}$-alkyl, —CONH$_2$, —CONH—$C_{1-3}$-alkyl-N(CH$_3$)$_2$, —O—$C_{2-3}$-alkyl-N(CH$_3$)$_2$ and —N(SO$_2$CH$_3$)($C_{1-3}$-alkyl-N(CH$_3$)$_2$), $R^{3.3.3}$ denotes H or methyl, $R^{3.3.4}$ denotes H or methyl, $R^{3.3.5}$ denotes H, $C_{1-3}$-alkyl or oxo, $R^{3.3.6}$ denotes H, oxo, —CH$_3$ or —CH$_2$—COO—CH$_3$, $R_{3.3.7}$ H, $C_{1-3}$-alkyl or oxo, $R^{3.2}$ and $R^{3.3}$ together with the nitrogen atom they are attached to form an optionally substituted 5- to 7-membered heterocycle, and $R^{3.4}$, $R^{3.5}$ independently from each other denote H or $C_{1-4}$-alkyl.

3. The compound of formula (I) according to claim 1, characterized in that

X denotes Cl, $R^1$ denotes H, and $R^2$ denotes H.

4. The compound of formula (I) according to claim 1, characterized in that $R^2$ denotes H, $R^3$ is selected from the group consisting of
—CN, —CH$_2$-morpholinyl, —PO(O—$R^{3.4}$)(O—$R^{3.5}$), —$C_{1-3}$-alkyl-S(O)$_2$OH, —$C_{1-4}$-alkyl-S(O)$_r$—$C_{1-6}$-alkyl, —$C_{1-3}$-alkyl-COOH, —$C_{1-3}$-alkyl-COOCH$_3$ and —CH$_2$—COO—$C_{1-3}$-alkyl, wherein $R^{3.4}$, $R^{3.5}$ independently from each other denote H or $C_{1-4}$-alkyl.

5. The compound of formula (I) according to claim 1, characterized in that $R^2$ denotes H, $R^3$ is selected from the group consisting of
$R^{3.1}$—OC(O)—, $R^{3.2}$N($R^{3.3}$)C(O)—, —$C_{1-3}$-alkyl-COOH, —$C_{1-3}$-alkyl-COOCH$_3$ and —CH$_2$—COO—$C_{1-3}$-alkyl, wherein $R^{3.1}$ denotes H, $C_{1-4}$-alkyl or phenyl-$C_{1-2}$-alkyl-, $R^{3.2}$ denotes H, methyl, ethyl or methoxyethyl, $R^{3.3}$ is selected from the group consisting of optionally substituted $C_{1-8}$-alkyl-optionally substituted $C_{3-8}$-cycloalkyl-, —$C_{2-8}$-alkyl-O—$C_{1-4}$-alkyl, hydroxy-$C_{2-4}$-alkyl-, optionally substituted —$C_{1-4}$-alkyl-phenyl-$R^{3.3.1}$ and —$C_{1-4}$-alkyl-5-to 7-membered heteroaryl-$R^{3.3.4}$, wherein $R^{3.3.1}$ and $R^{3.3.4}$ denote H.

6. The compound of formula (I) according to claim 1, characterized in that $R^2$ denotes H, $R^3$ denotes $R^{3.2}$N($R^{3.3}$)C(O)—, wherein $R^{3.2}$ denotes H or methyl, $R^{3.3}$ denotes optionally substituted —CH$_2$-phenyl-$R^{3.3.1}$, optionally substituted -phenyl-$R^{3.3.2}$, —$C_{1-4}$-alkyl-5-to 7-membered heteroaryl-$R^{3.3.4}$ or 5- to 7-membered heteroaryl-$R^{3.3.6}$, wherein $R^{3.3.1}$ denotes H or is selected from the group consisting of
—SO$_2$—$C_{1-3}$-alkyl, —SO$_2$—NH$_2$, —CONH$_2$ and -5-to 7-membered nonaromatic heterocycle-$C_{1-3}$-alkyl, $R^{3.3.2}$ denotes H or is selected from the group consisting of
—CO—N(CH$_3$)(nonaromatic heterocycle-$C_{1-4}$-alkyl), —N(SO$_2$—CH$_3$)(CH$_2$CONHCH$_3$), —N(COCH$_3$)($C_{1-4}$-alkyl-N(CH$_3$)$_2$), —N(CH$_3$)CO $C_{1-4}$-alkyl-N(CH$_3$)$_2$, —$C_{1-3}$-alkyl-nonaromatic heterocycle, —SO$_2$—N(CH$_3$)($C_{1-3}$-alkyl-N(CH$_3$)$_2$), —SO$_2$NH$_2$, —SO$_2$OH,
—COOH, —COO—$C_{1-3}$-alkyl, —CONH$_2$, —CONH—$C_{1-3}$-alkyl-N(CH$_3$)$_2$, —O—$C_{2-3}$-alkyl-N(CH$_3$)$_2$ and —N(SO$_2$CH$_3$)($C_{1-3}$-alkyl-N(CH$_3$)$_2$), $R^{3.3.4}$ denotes H or methyl, and $R^{3.3.6}$ denotes H or methyl.

7. A pharmaceutical composition comprising a compound according to claim 1 or a pharmaceutically acceptable salt thereof and a pharmaceutically acceptable carrier.

8. The pharmaceutical composition according to claim 7, further comprising active substances selected from among the categories of ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, cystic fibrosis transmembrane regulator (CFTR) correctors and CFTR potentiators or double or triple combinations thereof.

* * * * *